(12) United States Patent
Jang et al.

(10) Patent No.: US 9,884,183 B2
(45) Date of Patent: Feb. 6, 2018

(54) ACTIVE CARDIAC ELECTRICAL LEAD

(71) Applicant: SHANGHAI MICROPORT MEDICAL (GROUP) CO., LTD., Shanghai (CN)

(72) Inventors: Grace Ying Yang Jang, Shanghai (CN); Zhijun Cheng, Shanghai (CN)

(73) Assignee: SHANGHAI MICROPORT MEDICAL (GROUP) CO., LTD., Shanghai (CN)

( * ) Notice: Subject to any disclaimer, the term of this patent is extended or adjusted under 35 U.S.C. 154(b) by 0 days.

(21) Appl. No.: 14/419,934

(22) PCT Filed: Dec. 31, 2012

(86) PCT No.: PCT/CN2012/088075
§ 371 (c)(1),
(2) Date: Feb. 6, 2015

(87) PCT Pub. No.: WO2014/101200
PCT Pub. Date: Jul. 3, 2014

(65) Prior Publication Data
US 2015/0297883 A1 Oct. 22, 2015

(51) Int. Cl.
*A61N 1/05* (2006.01)
*A61N 1/362* (2006.01)

(52) U.S. Cl.
CPC ............ *A61N 1/056* (2013.01); *A61N 1/0565* (2013.01); *A61N 1/0573* (2013.01); *A61N 1/362* (2013.01)

(58) Field of Classification Search
CPC .............................. A61N 1/056; A61N 1/0565
See application file for complete search history.

(56) References Cited

U.S. PATENT DOCUMENTS

| 5,267,564 | A | * | 12/1993 | Barcel | A61N 1/056 600/310 |
| 5,514,172 | A | * | 5/1996 | Mueller | A61N 1/3752 600/396 |
| 5,545,200 | A | * | 8/1996 | West | A61B 18/1492 606/29 |
| 6,438,400 | B1 | * | 8/2002 | Beard | A61B 5/0421 600/380 |

(Continued)

FOREIGN PATENT DOCUMENTS

| CN | 102333561 A | 1/2012 |
| WO | 2009/078752 A1 | 6/2009 |

OTHER PUBLICATIONS

International Search Report for PCT/CN2012/088075.

*Primary Examiner* — George Evanisko
(74) *Attorney, Agent, or Firm* — Kilpatrick Townsend & Stockton LLP

(57) ABSTRACT

An active bipolar cardiac electrical lead includes a distal electrode (108), an intermediate connection mount (109), a ring electrode (103), and a tip housing (110). The intermediate connection mount (109) defines a proximal fitting (370) and a distal fitting (374). The ring electrode (103) has an exposed section (356) that sleeves over and engages the proximal fitting (370) of the intermediate connection mount (109) with a snap-fit connection. The intermediate connection mount (109) may connect the ring electrode (103) to the tip housing (110) and provide electrical insulation between the ring electrode (103) and the distal electrode (108).

5 Claims, 22 Drawing Sheets

(56) References Cited

U.S. PATENT DOCUMENTS

| | | |
|---|---|---|
| 2005/0246007 A1 | 11/2005 | Sommer et al. |
| 2009/0281592 A1 | 11/2009 | Vase |
| 2010/0222860 A1 | 9/2010 | Casella et al. |
| 2012/0040547 A1* | 2/2012 | Forslund ............... A61N 1/056 439/312 |

* cited by examiner

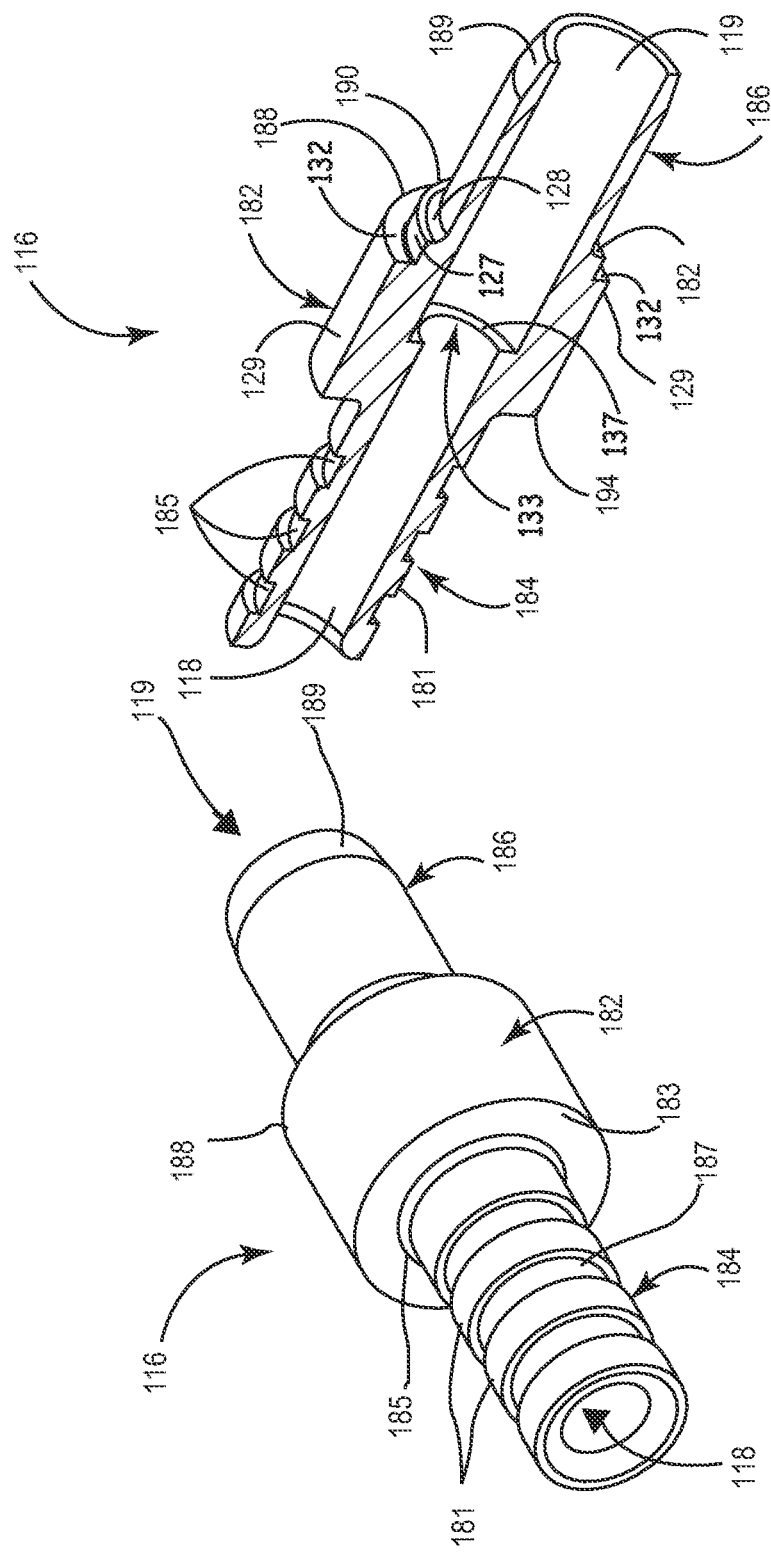

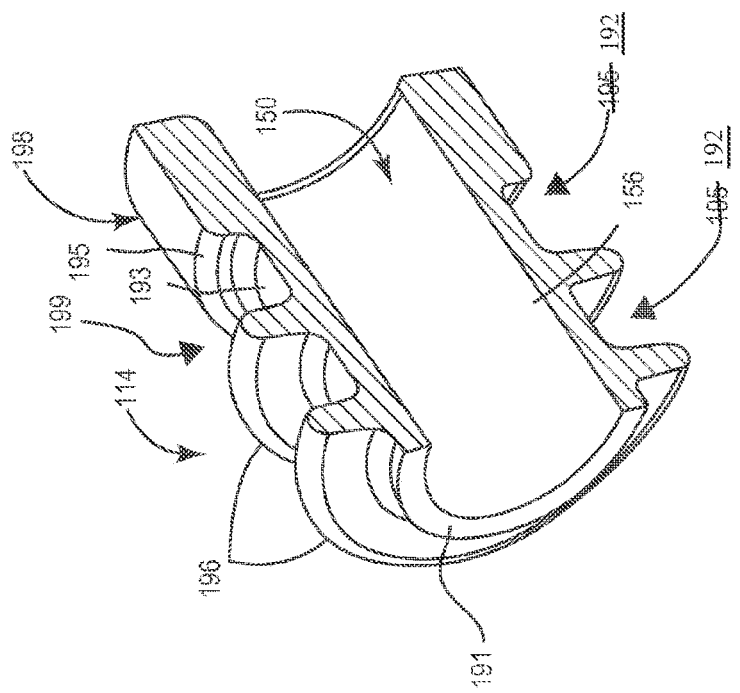
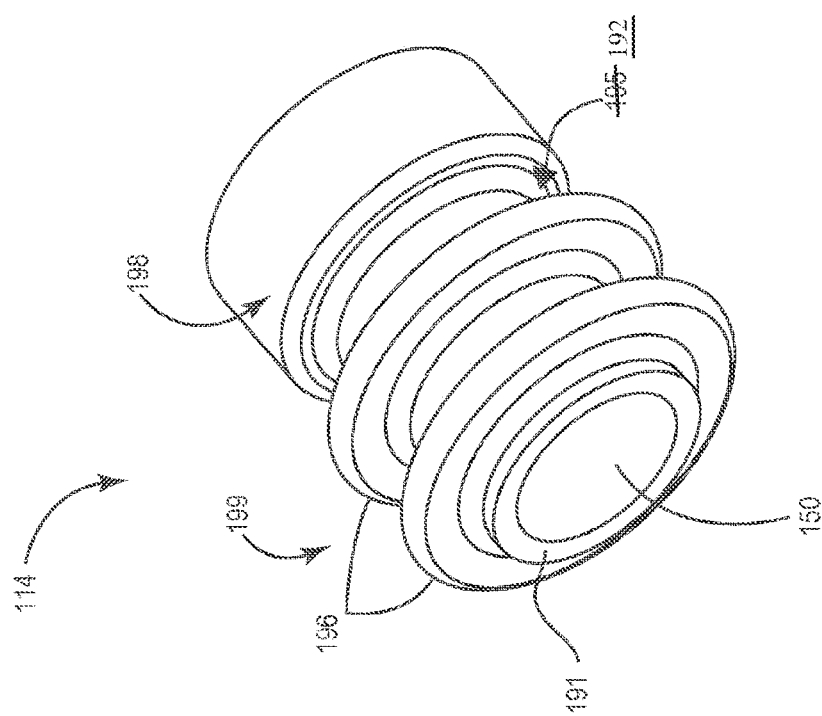
FIG.6A
FIG.6B

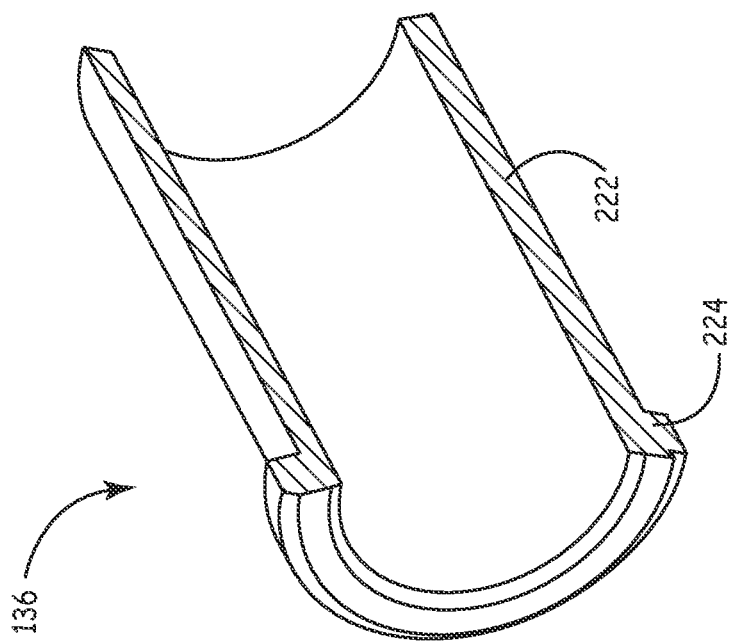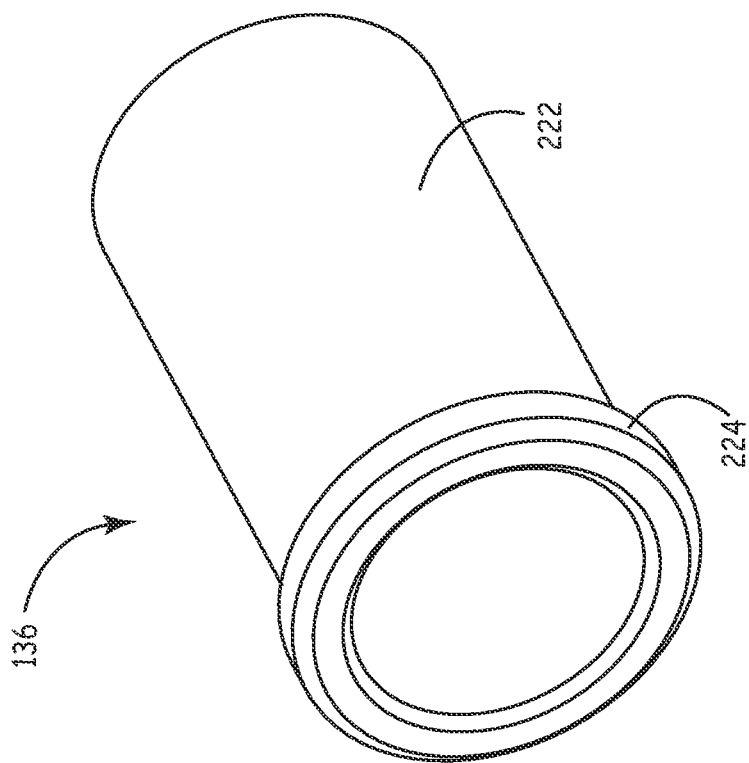

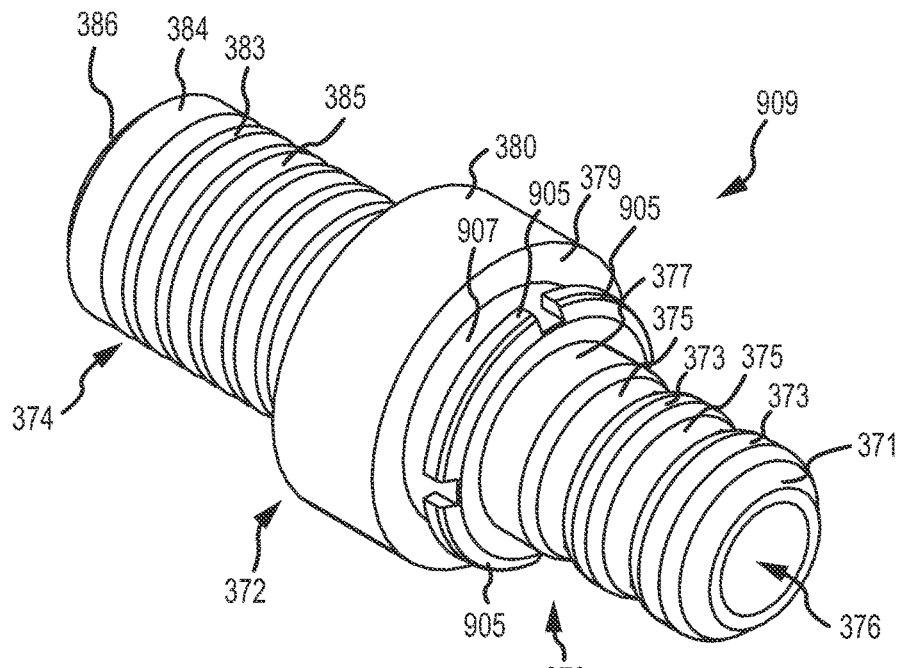
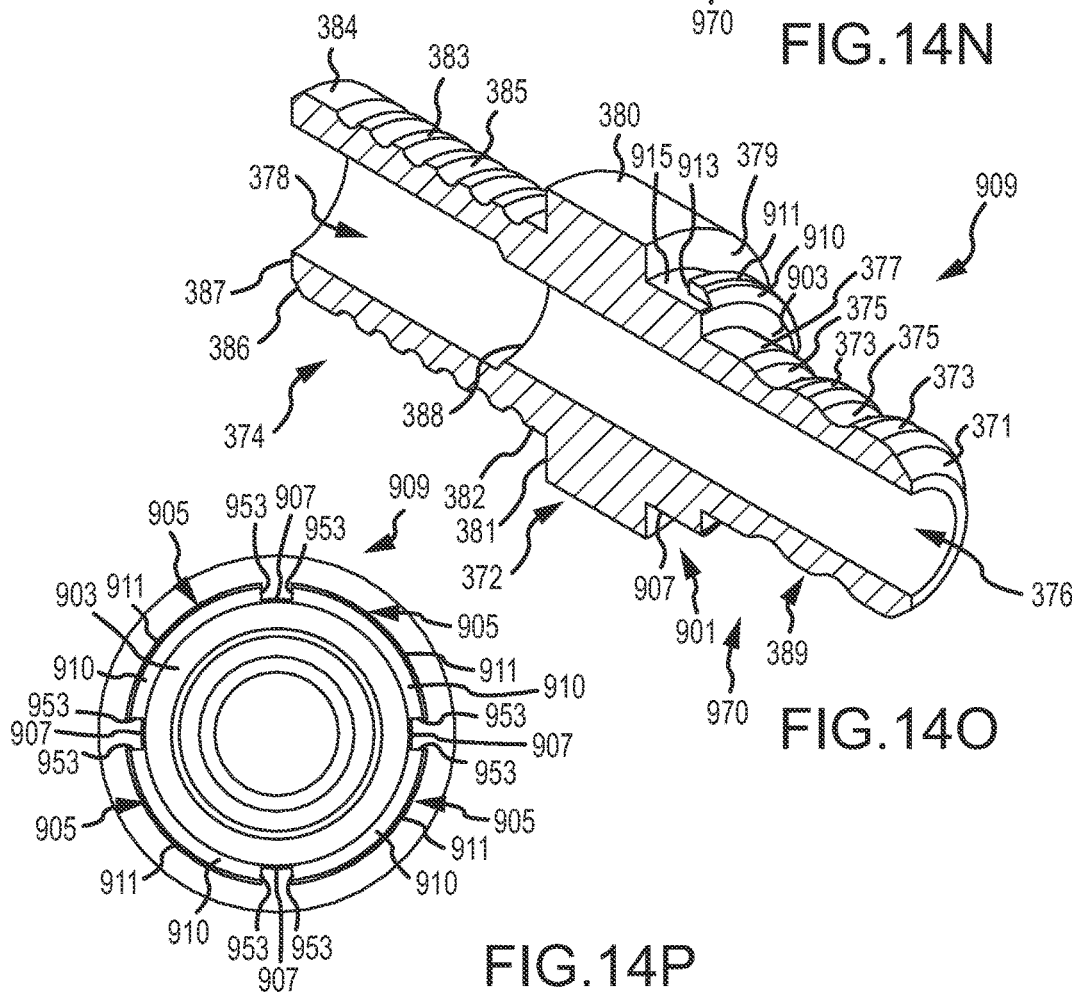

ACTIVE CARDIAC ELECTRICAL LEAD

This application is a US National Stage of International Application No. PCT/CN2012/088075, filed on Dec. 31, 2012, designating the United States, the content of which is hereby incorporated by reference in its entirety.

TECHNICAL FIELD

The present disclosure relates generally to implantable electrical leads. More particularly, the present disclosure relates to implant end features of implantable active electrical leads where the lead is connected to an associated defibrillator, pacemaker, or other electrical stimulation device.

BACKGROUND

Electrodes are often used to stimulate contraction of the heart. For example, when a patient's heart is functioning with an abnormal rhythm, electrical energy may be applied to the heart via the electrodes to return the heart to a normal rhythm. In some cases this procedure may be an isolated event while in other cases a more frequent, regular, or even continuous process is used. In these cases electrodes may be incorporated into a lead that is used with a pacemaker, defibrillator, or other electrical stimulation device such that pacing pulses may be delivered, for example, to an atrium or ventricle of a heart. The system including the electrical stimulation device and the lead may be implantable and, thus, used over long periods of time.

In general, a lead includes a pair of electrodes disposed at a distal end of the lead which may be positioned generally in the right ventricle or the right atrium of the heart. The proximal end of the lead may be coupled to a defibrillator or a pacemaker and conductors may deliver electrical impulses along the length of the lead to the electrode thereby delivering pacing pulses to the heart.

There are at least two conventional types of leads. The first type of leads is referred to as an active electrical lead with an active mechanism at the distal end. The second type of leads is referred to as a passive electrical lead with a passive mechanism at the distal end.

The distal end of a typical active electrical lead may include a helical anchor electrode designed to be actuated and axially extend and/or rotate out of a tip portion of the lead to engage or embed into the endocardium. The distal end of a typical passive electrical lead may include an anchor type fixation mechanism designed to anchor the distal end in the heart. The fixation mechanism for a passive lead, for example, may include one or more radially spaced tines that secure the distal end in the heart.

The proximal end of pacemaker and defibrillator leads are commonly designed and manufactured to a standard such as Chinese standard YY/T 0491-2004//ISO 5841-3, 2000. The standard is applicable to both active and passive pacemaker or defibrillator leads. Within that standard, medical device implant companies commonly have their own unique designs. Among the technologies used to meet the standard, are laser welding and metal crimping resulting in highly reliable pacemaker and defibrillator lead joint connections.

The design of defibrillator and pacemaker leads has evolved over time. Over time and at present, the proximal end of an active electrical lead and the proximal end of a passive electrical lead are generally designed differently due to their functional differences. That is, the proximal end of an active lead may be designed to actuate and/or control the distal active mechanism, while the proximal end of a passive lead may not include such actuation and/or control features. System designs and assembly processes of the passive and active electrical leads are, thus, different. As a result, the overall cost of having significant different system designs and assembly processes is relatively high and a system having common features or similar or exchangeable components between an active electrical lead and a passive electrical lead may be less expensive and more attractive to consumers.

The information included in this Background section of the specification, including any references cited herein and any description or discussion thereof, is included for technical reference purposes only and is not to be regarded subject matter by which the scope of the invention as defined in the claims is to be bound.

SUMMARY

In one implementation, an active bipolar cardiac electrical lead is provided. The lead may include a distal electrode, an intermediate connection mount, and a ring electrode. The intermediate connection mount may define a proximal fitting and a distal fitting. The ring electrode may have an exposed section configured to sleeve over and engage the proximal fitting of the intermediate connection mount in a snap-fit connection. The intermediate connection mount may connect the ring electrode to a tip housing surrounding the distal electrode and provide electrical insulation between the ring electrode and the distal electrode.

In another implementation, an intermediate connection mount for use with a distal end of an active cardiac lead is provided. The intermediate connection mount may be connectable with a ring electrode located proximally of the intermediate connection mount. The intermediate connection mount may include a medial separator, a distal fitting extending from the medial separator in a distal direction, and a proximal fitting extending from the medial separator in a proximal direction. The proximal fitting may include at least one radially-extending tab spaced from the medial separator in a distal direction to define an annular recess between the at least one tab and the medial separator.

In another implementation, a ring electrode for use with a distal end of an active cardiac lead is provided. The ring electrode may be connectable with an intermediate connection mount located distally of the ring electrode. The ring electrode may include a proximal sleeve forming a proximal end of the ring electrode and an exposed section located distally of the proximal sleeve. The exposed section may include an inner wall defining a bore configured to receive a portion of the intermediate connection mount. The inner wall may include an annular groove spaced proximally from a distal face of the ring electrode to define a radially inturned lip intermediate the distal face and the annular groove.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention is provided in the following written description of various embodiments of the invention, illustrated in the accompanying drawings, and defined in the appended claims.

BRIEF DESCRIPTION OF THE FIGURES

FIGS. 5A and 5B are an isometric view and an isometric cross-sectional view, respectively, of a connector insulator of the lead of FIGS. 1 and 2.

FIGS. 6A and 6B are an isometric view and an isometric cross-sectional view, respectively, of a proximal seal of the lead of FIGS. 1 and 2.

FIGS. 8A and 8B are an isometric view and an isometric cross-sectional view, respectively, of a ring sleeve of the lead of FIGS. 1 and 2.

FIGS. 14N, 14O, and 14P are an isometric view, an isometric cross-sectional view, and a proximal, elevation side view, respectively, of yet a further alternative intermediate connector mount.

DETAILED DESCRIPTION

The present disclosure relates to an implantable electrical lead having an active mechanism on a distal end (i.e., an active lead.) The active lead may include a system of parts on a proximal end thereof that is primarily adapted to connect to and electrically communicate with a defibrillator, pace maker, or other electrical stimulation device. It is noted that some of the parts may be adapted to insulate between other parts and/or between the proximal end and the electrical stimulation device. Additionally, a portion of the parts may be particularly adapted to allow actuation and control of the active mechanism on the distal end of the lead.

Figure 1:
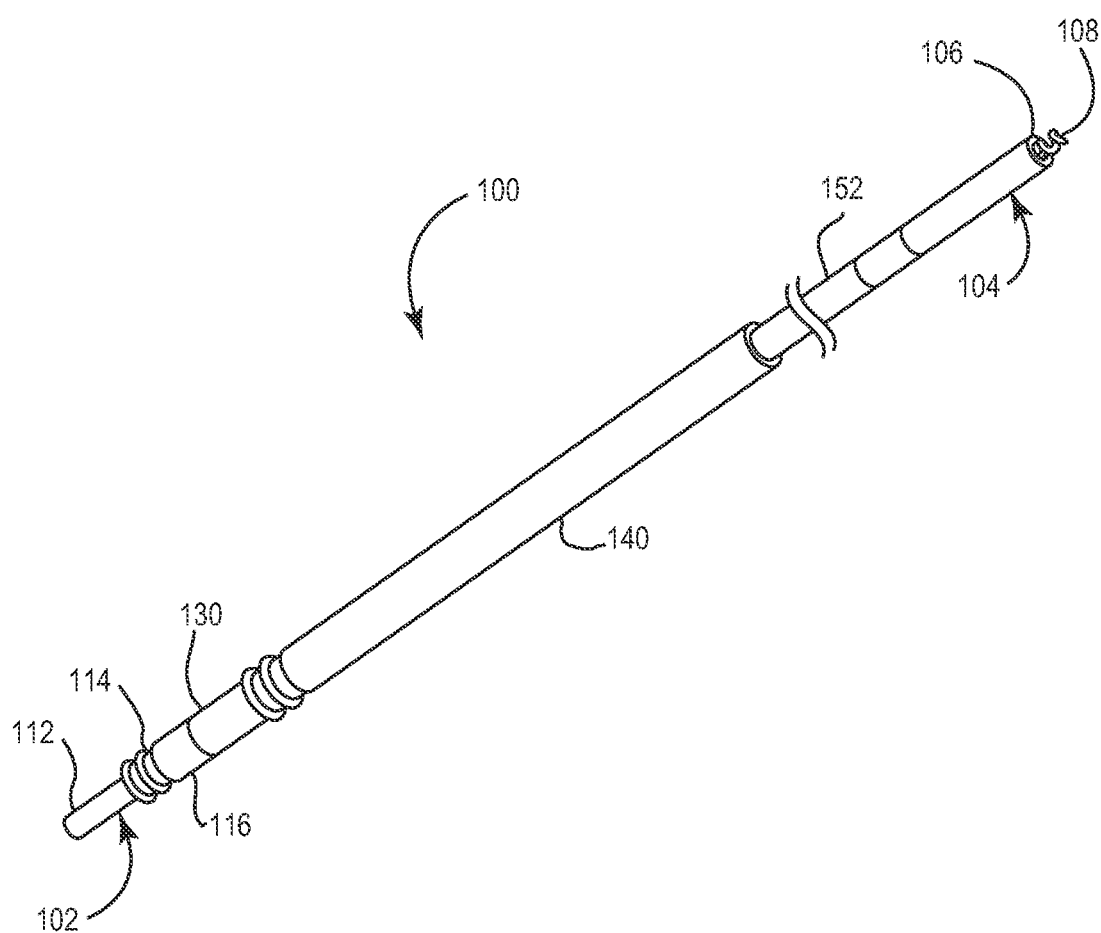
FIG. 1 is an isometric view of an exemplary embodiment of an implantable medical electrical lead with an active electrode.

FIG. 1 is an isometric view of one embodiment of an implantable medical electrical lead 100. The lead 100 has a proximal end 102 and a distal end 104. As shown, an active tip portion 106 may be disposed at the distal end 104 of the lead 100 and may include a distal electrode, for example, a helical anchor electrode 108. The helical anchor electrode 108 may be designed to axially extend out of the active tip portion 106 to engage a treatment site of a patient such as the endocardium of a heart, for example. The helical anchor electrode 108 may be retractably extended distally out of the active tip portion 106. In operation, a conductive connector pin at the proximal end 102 of the lead 100 may be rotated to drive a mechanism in the active tip portion 106, thereby extending the helical anchor electrode 108 out of the tip portion 106. The rotating extension of the helical anchor electrode 108 from the active tip portion 106 may engage (i.e., screw into) a treatment site of a patient.

Figure 2:
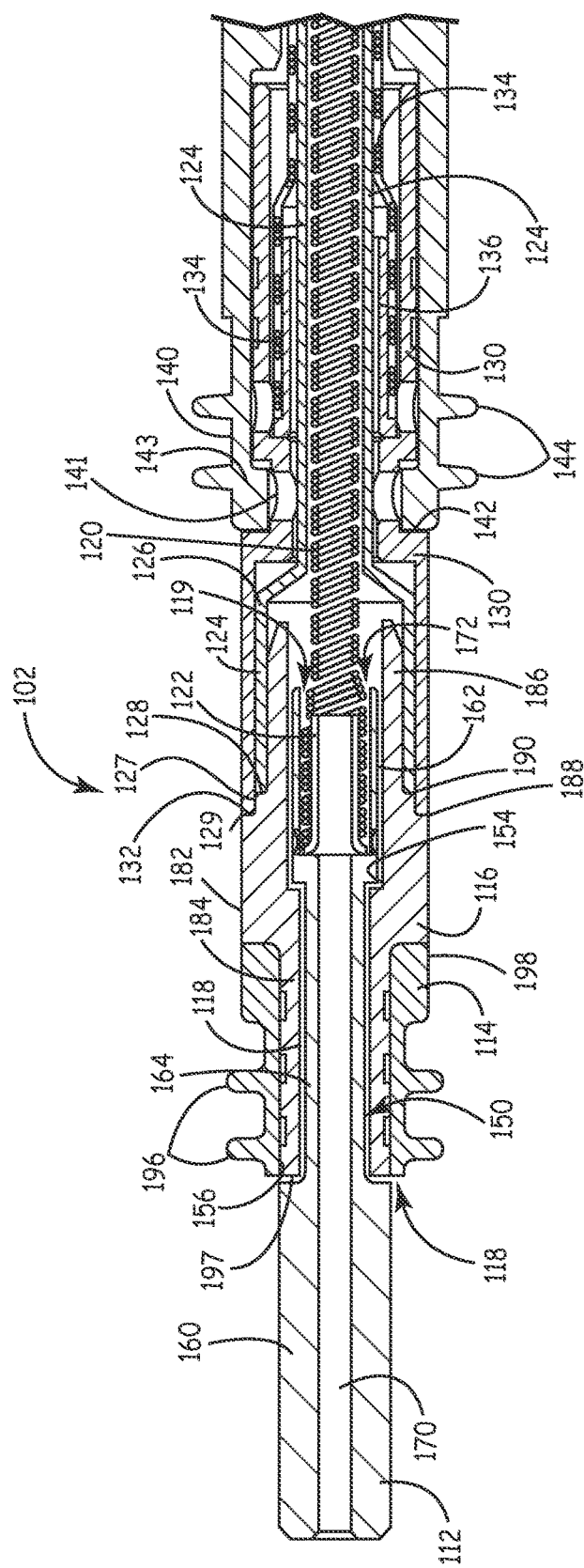
FIG. 2 is a cross-sectional view of a proximal end of the lead of FIG. 1.

Referring now to FIG. 2, the proximal end 102 of the lead 100 includes a system of parts or pieces. The system of parts or pieces may be divided into three categories including inner parts relating to an inner conductor, outer parts relating to an outer conductor, and insulating parts for electrically separating the inner parts from the outer parts. The inner parts may include a conductive connector pin 112, an inner conductor or coil 120, and a pin sleeve 122. The outer parts may include a ring connector 130, an outer conductor or coil 134, and a ring sleeve 136. The inner and outer parts may be substantially separated by the insulating parts including a connector insulator 116 and an insulator tubing 124. A proximal seal 114 and a boot seal 140 may also be provided.

Beginning with the inner parts, the connector pin 112 may be configured for electrical engagement with a defibrillator, pacemaker or other electrical stimulation device and for communicating electrical impulses to the inner conductor or coil 120. As such, the connector pin 112 may be adapted at one end for plugging into a socket of an electrical stimulation device and may be adapted at another end for connecting to the inner conductor or coil 120.

Figure 3:
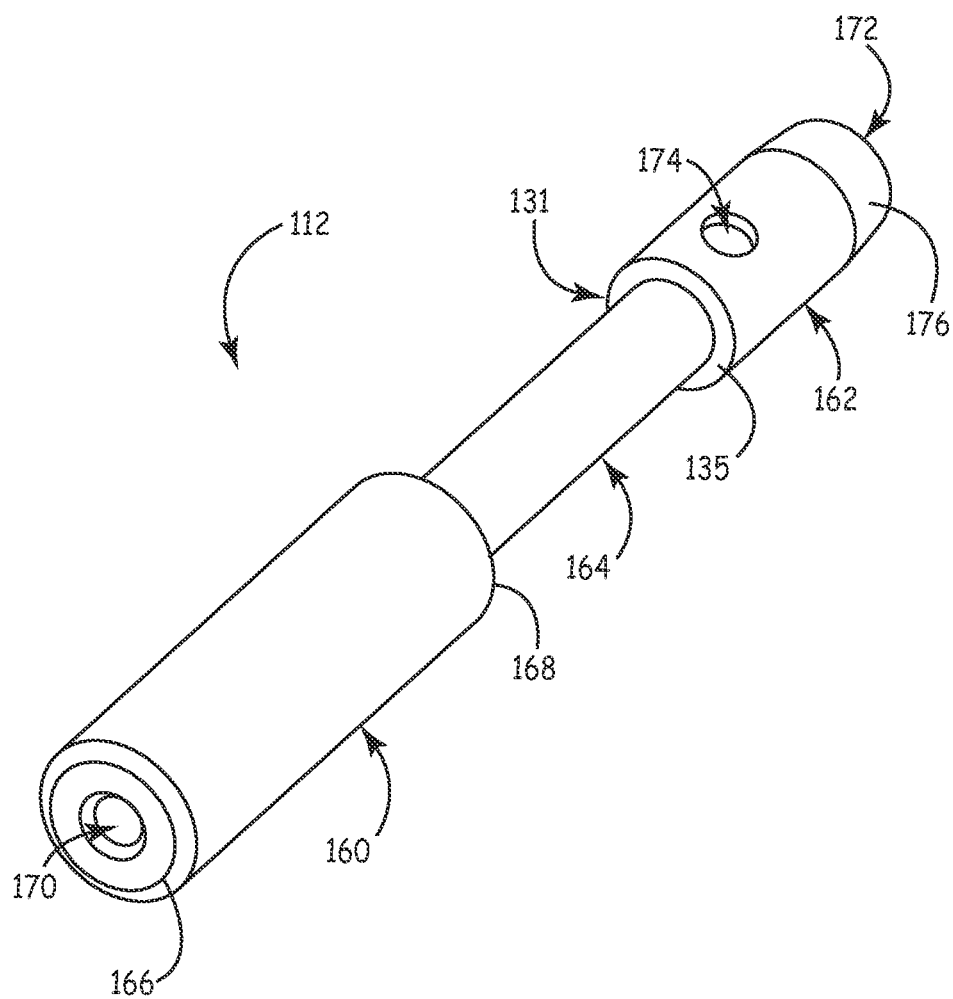
FIG. 3 is an isometric view of a connector pin of the lead of FIGS. 1 and 2.

A close-up view of a connector pin 112 is shown in FIG. 3. As shown, the connector pin 112 may include a socket end 160 and a conductor end 162 and may further include a bar portion 164 extending therebetween. The socket end 160 of the pin 112 may be generally elongate and cylindrically-shaped and may have a diameter adapted for placement in a correspondingly shaped socket of an electrical stimulation device. The proximal end of the socket end 160 may include a chamfered edge 166 for guiding the pin 112 into the socket when placing the pin 112 into the electrical device. The distal end of the socket end 160 may include a substantially sharp or square edge 168 for abutting the connector insulator 116 or the proximal seal 114 as the case may be.

Exposed portions of the proximal end 102 of the lead 100, like the socket end 160 just described, that may contact or otherwise physically interact with an electrical stimulation device, may be designed to meet industry standard specifications such as the IS-1 specification, for example. As such, while particular parts of the proximal end 102 are described herein as varying in size, diameter, length, or other dimensional variations, in some embodiments, the exposed portions of the parts may be selected to meet such specifications or standards. However, nothing in the present disclosure should be construed to limit the parts to industry standard dimensions.

The bar portion 164 of the connector pin 112 may also be generally elongate and cylindrically shaped and may have a diameter smaller than that of the socket end 160. The bar portion 164 may have a length selected to longitudinally secure the pin 112 relative to the connector insulator 116 and the proximal seal 114. That is, the length of the bar portion 164 may correspond to a bore length in the connector insulator 116 as shown in FIG. 2, such that longitudinal motion is substantially prevented relative to the connector insulator 116. As shown in FIG. 2, the socket end 160 and the bar portion 164 may include a longitudinally extending bore 170 extending from the socket end 160 of the pin 112 to the distal end of the bar portion 164 and exiting into a crimp zone 172 within the conductor end 162 of the pin 112. This bore 170 may be sized and adapted to receive a stylet, for example, when installing or positioning the lead 100, or when access to the distal end 104 of the lead 100 is desired.

The conductor end 162 of the pin 112 may be substantially cylindrically-shaped with an outer diameter slightly larger than that of the bar portion 164 and slightly smaller than that of the socket end 160. Other relationships of diameters of the several portions of the connector pin 112 may also be provided. For example, the conductor end 162 may have an outer diameter larger than the socket end 160. In the exemplary embodiment shown in FIG. 3, the conductor end 162 may be arranged in a relatively congested area where the ring connector 130, the insulator tubing 124, the connector insulator 116, the conductor end 162, the inner conductor 120, and the pin sleeve 122 all overlap. Where the proximal end 102 is designed to meet the IS-1 specification, for example, restrictions on the overall outer diameter together with the congestion may cause the outer diameter of the conductor end 162 to be smaller than the socket end 160.

The conductor end 162 of the pin 112 may include an inner cavity or crimp zone 172 having a substantially cylindrical cross-section with a diameter defining an inner diameter of the conductor end 162 as shown in FIG. 2. The conductor end 162 may have a length selected to match or exceed the length of the pin sleeve 122, to be described below, so as to provide suitable length for crimping the conductor 120. Other conductor end lengths may be selected and a suitable length of the cavity 172 may be selected to ensure sufficient crimp length of the coil 120 within the cavity 172.

The conductor end 162 may include a hole or a pair of holes 174 for inspecting the crimped conductor 120 within the cavity 172. The holes 174 may extend through the conductor end 162 from an outer surface and into the cavity 172 and may be positioned near a proximal end of the cavity 172. As such, when the conductor 120 is crimped in the cavity 172, a portion of the conductor 120 may be visible through the hole or holes 174 and the depth into the cavity 172 of the crimp connection may be ascertainable to assure sufficient crimp length.

The connector pin 112 can be made from one or more of several biocompatible conductor materials such as stainless steel 316L or a metal alloy, MP35N, for example. The pin material may be selected to be biocompatible and suitably conduct and transmit electrical signals from an electrical stimulation device. The material, together with the sizes of the pin 112 and the pin sleeve 122 (e.g., relative diameters and wall thicknesses), may be selected to suitably crimp the inner conductor or coil 120 therebetween such that a reliable crimp connection is provided that is both mechanically secure and through which electrical transmissions can be made. It is noted that the connector pin 112 may be engineered to have sufficient strength to withstand compression forces associated with assembly. For example, as can be appreciated from FIG. 2, the conductor end 162 of the pin 112 may be forced through the bore 118 of the connector insulator 116 into the bore 119 and the bar portion 164 of the pin 112 may be suitably strong to withstand such a compression force without buckling or weakening. In an effort to more smoothly insert the pin 112, the distal end of the conductor end 162 may include an exterior taper 176 as shown in FIG. 3.

Figure 4:
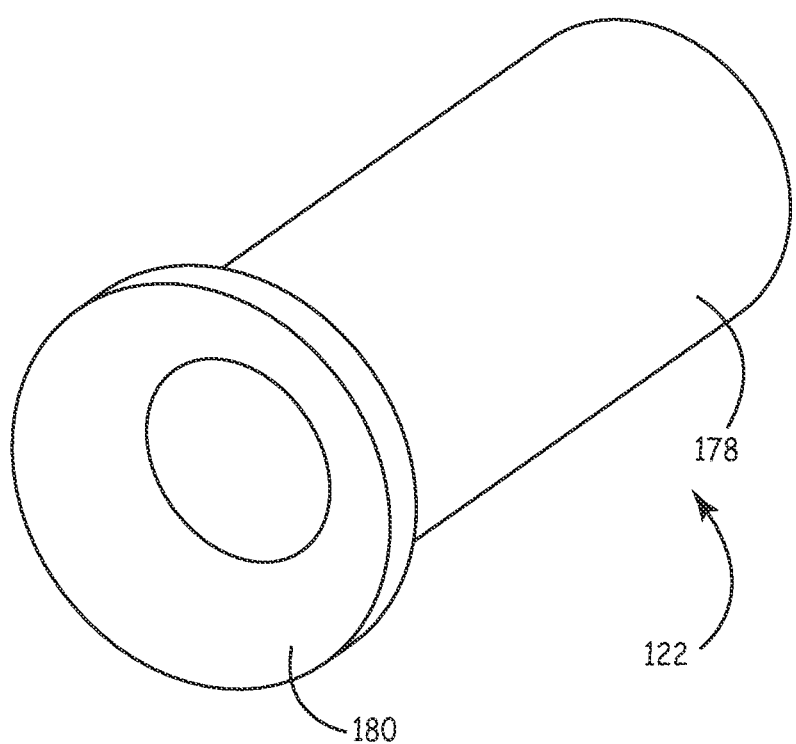
FIG. 4 is an isometric view of a pin sleeve of the lead of FIGS. 1 and 2.

An isolated view of the pin sleeve 122 is shown in FIG. 4. The pin sleeve 122 may be adapted for insertion a selected distance into the proximal end of the conductor or coil 120. As such, the pin sleeve 122 may include a sleeve portion 178 and a flare portion 180. The sleeve portion 178 may be substantially cylindrically shaped for insertion into the proximal end of the coil 120. The diameter of the sleeve portion 178 may be slightly larger than that of the coil 120 to create some connecting friction between the sleeve 122 and the coil 120 when the coil is sleeved over the sleeve portion 178. The diameter of the pin sleeve 122 may also be selected to suitably pinch or press the coil 120 against the inner surface of the cavity 172 of the conductor end 162 of the pin 112 when crimping the coil 120.

The sleeve portion 178 may have a length selected to sufficiently engage the coil 120 and hold the coil 120 when the coil 120 is crimped between the sleeve 178 and the inner surface of the conductor end 162 of the pin 112. The flare portion 180 of the sleeve 122 may be positioned on a proximal end of the sleeve 122 and may be configured to limit or stop the insertion distance of the sleeve 122 in the coil 120 and to prevent the sleeve 122 from passing too far into the coil 120 when crimping the coil 120. As such, the flared portion 180 may define a gradually increasing diameter beginning with the diameter of the sleeve portion 178 and extending to a diameter approximating the inner diameter of the crush cavity 172 of the conductor end 162 of the pin 112. It is noted that the proximal end of the pin sleeve 122 is shown as a flared portion in contrast to the more square or flange-like proximal end on the ring sleeve 136 of FIGS. 8A and 8B. The shape of the proximal ends of the pin sleeve 122 and ring sleeve 136 may be selected based on whether the respective part is formed from tubing or bar stock. For example, if the part is formed from tubing, the proximal end may be flared like the pin sleeve 122 shown.

However, if the part is formed from bar stock, the proximal end may be machined to be flanged like the ring sleeve 136. Other fabrication techniques and approaches may also be used.

The inner diameter of the conductor end 162 of the pin 112 and the outer diameter of the sleeve portion 178 of the pin sleeve 122 may be selected to suitably crimp the inner conductor or coil 120 therebetween. For example, the pin sleeve 122 may have an outer diameter and the wire used for the inner coil 120 may have a thickness. The inner diameter of the cavity 172 may be selected to be slightly less than the outer diameter of the pin sleeve 122 plus twice the wire thickness. As such, when the pin sleeve 122 is inserted into the coil 120 and the pin sleeve 122 and conductor 120 are pressed into the cavity 172 of the conductor end 162 of the pin 112, the coil 120 may be crimped between the pin sleeve 122 and the inner surface of the cavity 172 of the conductor end 162 of the pin 112. Consideration may be given to the thicknesses and elasticity of the conductor end 162 of the pin 112 and the pin sleeve 122 when selecting suitable relative diameters.

The inner conductor or coil 120 may be an electrically conductive member extending longitudinally along the lead 100. The conductor 120 may be in the shape of a coil or a tubular sleeve shape may be provided. The coil shape may provide flexibility to the lead and allow for maneuverability when placing the lead, for example. The inner conductor 120 may define a longitudinally extending bore along its length for receiving a stylet or other device.

As mentioned, the inner parts may be electrically isolated from the outer parts by a system of insulating parts. A close-up view of the connector insulator 116 is shown in FIGS. 5A and 5B. The connector insulator 116 may be configured for sleevably isolating the connector pin 112 and a portion of the inner conductor 120 from the outer parts. In addition, the connector insulator 116 may be configured for supporting a portion of the proximal seal 114. The connector insulator 116 may be configured to separate the connector pin 112 from the proximal seal 114 such that the connector pin 112 may be easily rotated, thereby rotating the inner conductor or coil 120 and controlling a tip electrode pin 105 and the helical anchor electrode 108 attached thereto on a distal end 104 of the lead 100 as shown in FIG. 10B. The connector insulator 116 may include a central body 182, a proximal extension 184, and a distal extension 186. The central body 182 may include a substantially cylindrically-shaped body having an outer diameter. The distal extension 186 may also be substantially cylindrically-shaped and may include an outer diameter smaller than that of the central body 182.

The distal extension 186 may extend from the central body 182 in the distal direction from a set of cascading shoulders 188, 190. An outer shoulder 188 may be defined by the interface of a portion of the outer surface 129 of the central body 182 and a step surface 132. The inner width 190 may be defined by a cylindrical inner shoulder surface 127 intersecting normally with the step surface 132 and transitioning to an additional radially oriented step surface 128. The width of the step surface 132 may define the difference between a diameter of a cylindrical inner shoulder surface 127 and the diameter of the central body. The diameter of the inner shoulder surface 127 is less than the diameter of the central body 182 but larger than the diameter of the distal extension 186. The width of the additional step surface 128 may define the difference between the diameter of the inner shoulder surface 127 and the diameter of the distal extension 186.

The distal tip of the distal extension 186 may include a tapered or chamfered tip 189 creating a conical shape for receiving a dilated portion 126 of the insulator tubing 124. As shown in FIG. 2, for example, the dilated portion 126 of the insulator tubing 124 may be stretched, expanded, or otherwise distended over the distal extension 186 of the connector insulator 116. The dilated portion 126 is held away from the crimp connection of the inner conductor 120 to provide space for this connection and may help to avoid binding, pinching, or otherwise constricting the crimp connection at this location.

The proximal extension 184 of the connector insulator 116 may extend from the proximal end of the central body 182 and may be substantially cylindrical with a diameter smaller than that of the central body 182. The transition between the central body 182 and the proximal extension 184 may define a proximal shoulder 183 opposite the cascading shoulders described. The interface between the proximal extension 184 and the proximal shoulder 183 may be formed as a small, concave, annular radius 185. The outer surface of the proximal extension 184 may be formed as a plurality of alternating flat annular ribs 181 and flat annular channels 187. The proximal extension 184 may extend underneath the proximal seal 114. As such, when the proximal seal 114 is positioned on the proximal extension 184, a distal end of the proximal seal 114 may abut the proximal shoulder 194 of the central body 182 and a proximal end of the proximal seal 114 may align with the proximal end of the connector insulator 116.

The connector insulator 116 may include center bore 118 with a diameter configured for receiving the bar portion 164 of the connector pin 112. The diameter of the bore 118 may be slightly larger than the bar portion 164 so as to allow rotation of the connector pin 112 relative to the connector insulator 116. In other embodiments lubrication and/or a bushing may be provided to offer further rotational freedom of the pin 112 relative to the connector insulator 116. The center bore 118 may extend from the proximal end of the insulator 116 to a point within the central body 182 of the insulator 116 where the center bore 118 may transition to a bore 119 with a larger diameter. The bore 119 with the larger diameter may accommodate the increased diameter of the conductor end 162 of the connector pin 112. The diameter of the bores 118, 119 may remain slightly larger than the respective portion of the connector pin 112. The bore 119, with its larger diameter, may extend through the remaining portion of the central body 182 and through the distal extension 186 of the connector insulator 116.

The connector insulator 116 may be constructed from a bio-compatible grade of insulator material. This material may be selected to provide sufficient mechanical strength, elasticity, and insulation characteristics. For example, as described with respect to the connector pin 112, the conductor end 162 of the connector pin 112 may be pressed through the bore 118 of the connector insulator 116. As such, the connector insulator 116 may be made of a relatively strong yet elastic material allowing the pin 112 to be driven therethrough without loss of strength and without permanent deformation. In some embodiments, the connector insulator 116 may be made from a moldable thermoplastic such as polyurethane, polysulfone, or PEEK. Still other material may be selected to provide the suitable strength, elasticity, and insulation characteristics.

While elastic, the connector insulator 116 may also be designed to secure the connector pin 112 and prevent the connector pin 112 from being removed or withdrawn from the proximal end of the lead 100. A proximal shoulder 131 at the proximal end of the conductor end 162 may be provided to transition to the smaller diameter bar portion 164 (See FIG. 3.). A surface 135 of the shoulder 131 may interact with an opposing surface 137 of shoulder 133 on the interior surface of the connector insulator 116. (See FIG. 2.) The shoulder 133 on the interior of the connector insulator 116 may be formed as the transition between the bore 118 and bore 119. The relative diameters of the bar portion 164 and bore 118 and the relative diameters of the conductor end 162 and bore 119 may be selected to allow the connector pin 112 to rotate within the connector insulator 116. However, to prevent removal therefrom, the diameter of the conductor end 162 may be selected to be larger than the diameter of the bore 118. In addition, the material of connector insulator 116 may be selected to be rigid enough to prevent withdrawal of the connector pin 112 under withdrawal loads or strengths specified by the IS-1 specification, for example.

The proximal seal 114 may be configured for secured placement on the connector insulator 116 and for sealingly engaging a socket on an electrical stimulation device. In addition, the proximal seal 114 may function, together with the connector insulator 116, to electrically isolate and prevent crosstalk between the ring connector 130 and the connector pin 112. As shown in FIGS. 6A and 6B, the proximal seal 114 may include a flush portion 198 and a seal portion 199. The flush portion 198 may be distal to the seal portion 199 and may function to encompass the proximal extension 184 of the connector insulator 116 and abut the central body 182 thereof. The flush portion 198 may be substantially cylindrical with an outer diameter substantially matching the outer diameter of the central body 182 of the connector insulator 116 thereby being flush therewith. The seal portion 199 may be proximal to the flush portion 198 and may also be substantially cylindrical with an outer diameter slightly larger than the flush portion 198. The seal portion 199 may include one or more (e.g., two) annular, radially-extending ribs 196 protruding from the outer surface of the seal portion 199 and defining relatively deep channels 195 in between. The ribs 196 may extend from the seal portion 199 such that the outer surface or tip of the ribs 196 defines a diameter larger than the flush portion 198. The diameter of the channels 192 may be smaller than the diameter of the flush portion 198 such that there is a stepped shoulder 195 between a base wall 193 of the channel 192 and the flush portion 198. A proximal annular lip 191 of the proximal seal 114 may have a similar diameter to the diameter of the channels 192 at the base wall 193 and may extend proximally as an annular ring from the most proximal rib 196. The ribs 196 may be adapted to engage a cylindrical socket and may have an outer diameter at least slightly larger than the diameter of the socket so as to sealingly engage an inner surface of the socket and prevent fluids or other matter from traveling into the socket and reaching the connector pin 112 or otherwise leaking into the electrical stimulation device.

The proximal seal 114 may include a bore 150 of constant diameter extending from the proximal end to the distal end. The bore 150 may be sized to seal against the outer diameter of the proximal extension 184 of the connector insulator 116. The diameter of the bore 150 may be substantially equal to the outer diameter of the proximal extension 184 of the connector insulator 116. The inner surface 156 of the bore 150 may further be fixed to the proximal extension 184 of the connector insulator 116 by a medical adhesive or other bioadaptable adhesive equivalent.

In some embodiments, the proximal seal 114 may be made of a resilient material and the diameter of the bore 150 may be slightly smaller than the outer diameter of the proximal extension 184 of the connector insulator 116 such that the proximal seal may be stretched to receive the connector insulator 116 thereby compressively receiving the connector insulator 116 therein. The proximal seal 114 may be made from a suitably resilient material to compressively seal the proximal end 102 of the lead 100 with the electrical stimulation device. In some embodiments, the seal 114 may be a biocompatible silicone, for example. Still other materials may be selected to suitably seal the proximal end 102 of the lead 100 with the electrical stimulation device and also be compatible with the body.

The insulator tubing 124 shown in FIG. 2 may function to electrically isolate portions of the inner parts from the outer parts. Along some portions of the lead 100, the insulator tubing 124 may function together with the connector insulator 116 to provide the electrical isolation. As shown, conductive portions of each of the inner parts, including the conductor end 162 of the connector pin 112, the inner coil 120, and the pin sleeve 122, may be separated from the outer parts by the inner insulator tubing 124. Near the proximal end of the conductor 120, the distal extension 186 of the connector insulator 116 also isolates these elements. The insulator tubing 124 may be substantially tube-like in shape defining an inner lumen having a diameter slightly larger than the outer diameter of the inner conductor or coil 120. As such, in the case of an active lead, the inner conductor 120 may be relatively free to rotate within the insulator tubing 124. The insulator tubing 124 may be made of an insulating material so as to electrically isolate the enclosed components or features from the components or features outside the tubing 124.

The insulator tubing 124 may include a flared portion 126 at its proximal end for receiving the distal extension 186 of the connector insulator 116. In some embodiments, the flared portion 126 is expanded to fit over the distal extension 186 of the connector insulator 116. The flared portion 126 may be held open by the distal extension 186 of the connector insulator 116 and may help to prevent binding of the inner parts by providing space for the crimp connection. Within the distal extension 186 of the connector insulator 116, the conductor end 162 of the pin connector 112, the pin sleeve 122, and the proximal end of the conductor or coil 120 may be arranged and thus electrically isolated from components or features outside the portion 126.

Having described the inner parts and the isolation thereof by the insulator tubing 124 and the connector insulator 116, the outer parts may now be described. As shown in FIG. 2, the outer parts may include the ring connector 130, an outer conductor or coil 134, and a ring sleeve 136.

The ring connector 130 may be configured to provide an exposed surface for electrical communication with an electrical stimulation device. The ring connector 130 may also be configured for axially and rotationally securing the outer parts to the connector insulator 116.

Figure 7B:
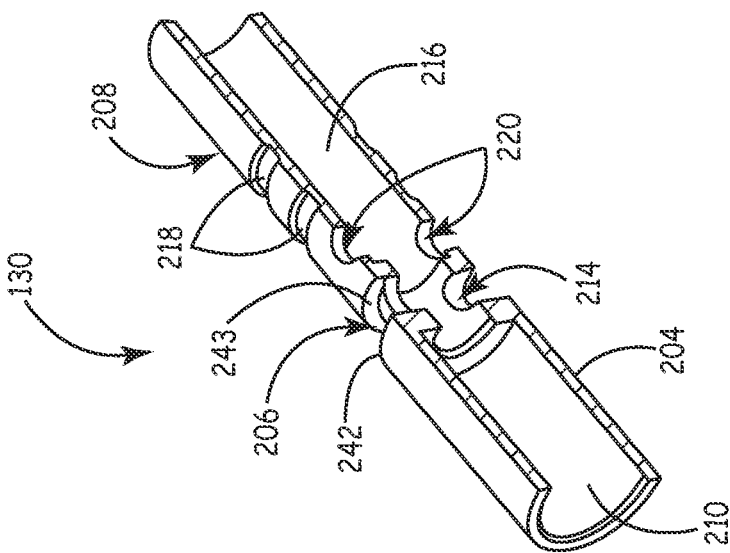
FIGS. 7A and 7B are an isometric view and an isometric cross-sectional view, respectively, of a ring connector of the lead of FIGS. 1 and 2.
Figure 7A:
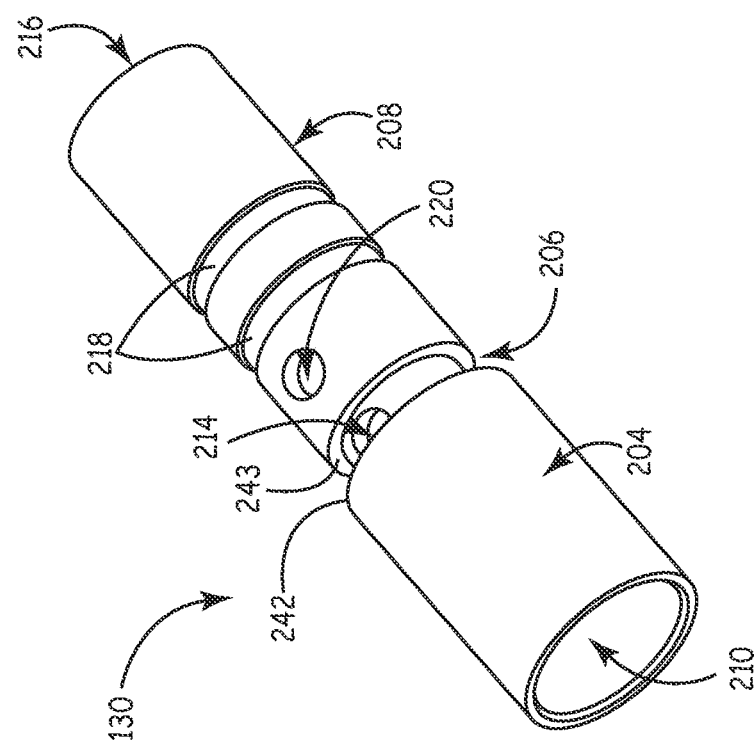

An isolated view of the ring connector 130 is shown in FIGS. 7A and 7B. The ring connector 130 may include a band portion 204, a slot portion 206, and a crimp portion 208. The band portion 204 may form an exposed conductive band near the proximal end 102 of the lead 100 that is distal to the connector pin 112. The band portion 204 may be configured for electrical communication with a portion of a socket of an electrical stimulation device and the diameter of the band portion 204 may be selected to suitably engage electrical conductors within the socket.

The band portion 204 may be substantially cylindrical in shape with an outer diameter matching that of the central body 182 of the connector insulator 116. The band portion 204 may define an inner cavity 210 configured to receive the distal extension 186 of the connector insulator 116. More particularly, the inner cavity 210 of the band portion 204 may have a diameter substantially equal to or slightly smaller than the outer diameter of the cylindrical inner shoulder surface 127 on the connector insulator 116. As such, the band portion 204 may be sleeved over the flared portion 126 positioned on the distal extension 186 and may frictionally engage the cylindrical inner shoulder surface 127 to secure the ring connector 130 to the connector insulator 116. In this manner, the concentric assembly of the several parts of the system may be maintained. The proximal edge of the band portion 204 of the ring connector 130 may thus abut the step surface 132 of the connector insulator 116 causing the outer surface of the band portion 204 to be flush with the central body 182 of the connector insulator 116. The band portion 204 may have a length slightly greater than the length of the distal extension 186 of the connector insulator 116.

The slot portion 206 of the ring connector 130 is distal relative to the band portion 204 and is positioned intermediate the band portion 204 and the crimp portion 208. The slot portion 206 may be substantially cylindrical in shape with a diameter smaller than the band portion 204. The slot portion 206 may have an inner diameter similar to or slightly larger than the outer diameter of the insulator tubing 124, whereby the slot portion 206 is configured to engage in a tight fit with the insulator tubing 124. The outer diameter of the slot portion 206 may allow for an inwardly projecting rib 143 from the boot seal 140 to nest therein as further described below. The rib 143 may be held in position longitudinally by two opposing surfaces 242 and 243 defining the boundaries of the slot portion 206. The slot portion 206 may include one or more holes 214 for introduction of adhesive to secure the ring connector 130, the insulator tubing 124, and the boot seal 140 together.

The crimp portion 208 may be arranged distally to the slot portion 206 and may be substantially cylindrical in shape with an outer diameter larger than the slot portion 206 and smaller than the band portion 204. Like the conductor end 162 of the connector pin 112, the crimp portion 208 of the ring connector 130 may be configured for crimping the outer conductor 134 therein. As such, the crimp portion 208 may define a crimp zone or cavity 216 therein. The cavity or crimp zone 216 may include an inner diameter selected in conjunction with the ring sleeve 136 to suitably crimp the outer conductor 134 therein. That is, the ring sleeve 136 may have an outer diameter and the outer conductor 134 may include a wire thickness. The inner diameter of the crimp zone or cavity 216 may be selected to be equal to or slightly smaller than the outer diameter of the ring sleeve 136 plus twice the wire thickness, for example.

Like the inner conductor crimp connection, the material strength, diameter, thickness, and elasticity may be considered when selecting the relative diameters for crimping the outer conductor 134. The crimp portion 206 of the ring connector 130 may have a length equal to or slightly larger than the ring sleeve 136 such that a sufficient length of the outer conductor 134 may be crimped therein. In some embodiments the crimp portion 208 of the ring connector 130 may include circumferentially extending grooves 218 extending around its circumferential outer surface for engagement with the boot seal 140. The crimp portion 208 may also include a hole or a pair of holes 220 for inspecting the crimped conductor 134 within the cavity 216 and confirming the quality of the connection. The holes 220 may extend through the crimp portion 208 from an outer surface and into the cavity 216 and may be positioned near a proximal end of the cavity 216. As such, when the conductor 134 is crimped in the cavity 216, a portion of the conductor 134 may be visible through the hole or holes 220 and the crimp connection may be ascertainable to assure sufficient crimp length.

Like the connector pin 112, the ring connector 130 may be constructed of a bio-compatible conductive material. For example, the ring connector 130 may be made from stainless steel 316L or a metal alloy MP35N. Other materials may also be used and may be selected to provide suitable biocompatibility and conductivity. Additionally, as with the connector pin 112, the material and dimensions (e.g., relative diameters and wall thicknesses) may be selected to suitably allow for a crimp connection to the outer conductor or coil 134 that is both mechanically secure and also effectively transmits electrical signals.

The outer conductor or coil 134 may be the same or similar to the inner conductor or coil 120. However, the outer conductor or coil 134 has a diameter larger than the inner conductor or coil 120. The diameter of the outer conductor or coil 134 may be selected such that the inner conductor or coil 120 and the insulator tubing 124 may be received therein. As such, the outer conductor or coil 134 may have a diameter equal to or slightly greater than an outside diameter of the inner conductor or coil 120 plus twice the thickness of the insulator tubing 124. In some embodiments, the diameter of the outer conductor or coil 134 may be selected to allow non-constricted rotation of the inner coil 120 within the insulator tubing 124 for controlling an active mechanism 106 on a distal end 104 of the lead 100, for example. In other embodiments, the diameter of the outer coil 134 may be more constricting on the insulator tubing 124 and the inner coil 120.

The ring sleeve 136, like the pin sleeve 122 may be configured for crimping the outer conductor or coil 134 within the crimp portion 208 of the ring connector 130. As shown in FIGS. 8A and 8B, the ring sleeve 136 may be formed as a cylindrical sleeve portion 222 with a flare or flange portion 224 for controlling the depth within the coil 134 that the ring sleeve 136 extends. The sleeve portion 222 may be substantially cylindrical with an outer diameter slightly larger than an inner diameter of the outer coil 134. As such, when inserted into a proximal end of the outer coil 134, some frictional engagement between the ring sleeve 136 and the outer coil 134 may be provided. The flare or flange portion 224 may be positioned on the proximal end of the sleeve portion 222 and may have an outer diameter larger than that of the sleeve portion 222 for abutting the end of the outer conductor or coil 134 and resisting advancement of the ring sleeve 136 beyond the proximal end of the outer conductor or coil 134. The diameter of the flare or rib 224 may be selected to be slightly less than the inner diameter of the crimp portion 208 of the ring connector 130 so as to avoid inhibiting the pinching or crimping of the coil 134 between the sleeve portion 222 and the inner surface of the crimp portion 208 of the ring connector 130. As discussed with respect to the pin sleeve 122, the shape of the proximal end of the pin sleeve 122 and the ring sleeve 136 may depend in part on the type of raw material used to form the respective part. For example, if tubing is used, the proximal end may be flared, while, if bar stock is used, the proximal end may be more square in cross-section or flange-like. Other geometries may also be provided to stop the sleeves from advancing too far into the proximal end of the respective coils 120, 134.

Figure 9A:
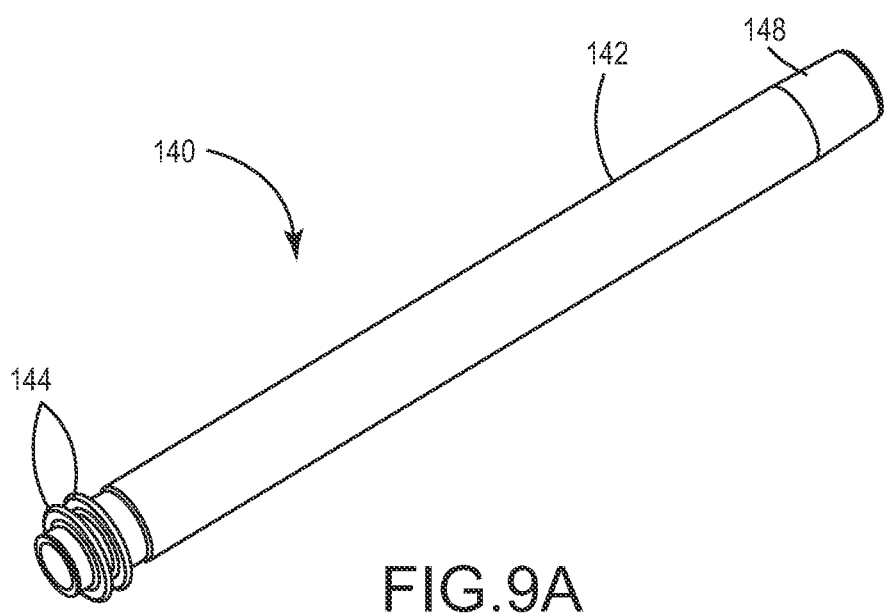
FIGS. 9A and 9B are an isometric view and an isometric cross-sectional view, respectively, of a boot seal of the lead of FIGS. 1 and 2.
Figure 9B:
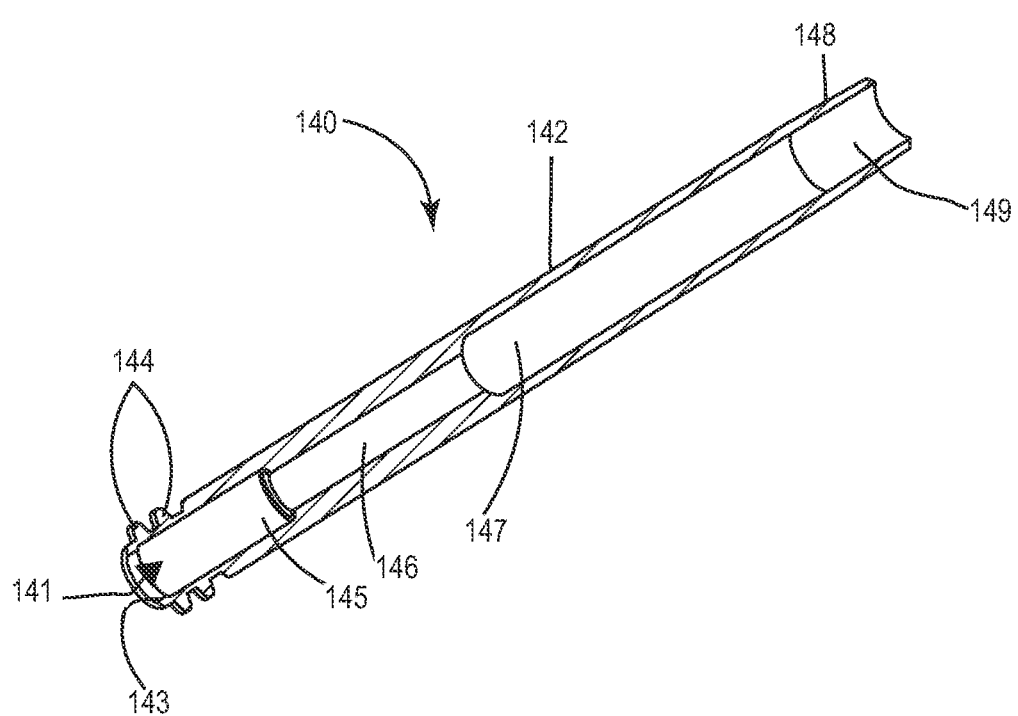

The boot seal 140 is shown in FIGS. 9A and 9B. The boot seal 140 may be configured for encompassing and sealing against the distal end of the ring connector 130 and the proximal end of the outer sheath 152 to prevent entry of fluids. For example, when the proximal end 102 of the lead 100 is inserted into a socket of an electrical stimulation device, the boot seal 140 may prevent fluids or other material from entering the socket and interfering with the ring connector 130 or other portions of the electrical stimulation device. As such, the boot seal 140, like the proximal seal 114, may have one or more annular, radially-extending sealing ribs 144 protruding from its outer surface at its proximal end. The sealing ribs 144 may be adapted to engage a cylindrical socket and may have an outer diameter at least slightly larger than the diameter of the socket so as to sealingly engage an inner surface of the socket and prevent fluids or other matter from traveling into the socket and reaching the ring connector 130 or otherwise leaking into the electrical stimulation device. The boot seal 140 may be relatively long with a cylindrical shaft portion 142 that extends distally from the sealing ribs 144 and may provide a grip for the surgeon or other installer for handling the proximal end 102 of the lead 100. The cylindrical shaft portion 142 may taper radially inward at the distal end of the boot seal 140 to form a chamfered portion 148.

The boot seal 140 may define a bore 141 extending from its proximal end to its distal end. The diameter of the bore may vary along the length of the seal 140. The diameter of a proximal section 145 of the bore 141 may be sized to house the crimp portion 208 of the ring connector 130. Moving distally, the diameter of the bore 141 throughout a medial section 146 may be reduced and may be sized just slightly larger than the outer diameter of the outer coil 134. Moving still further distally, the diameter of a distal section 147 of the bore 141 may again be enlarged with respect to the medial section 146. In this distal bore section 147, the boot seal 140 may be enlarged to receive the outer insulating sheath 152 and for the application of a lead label and/or serial number. The bore 141 within the chamfered portion 148 at the distal end of the boot seal 140 may also be tapered slightly radially inward to form a tapered seal portion 149 that creates the fluid tight seal around the outer sheath 152. The proximal end of the boot seal 140 may define an annular securing rib 143 protruding inwardly for positioning in the slot portion 206 of the ring connector 130, thereby securing the axial position of the boot seal 140. Like the proximal seal 114, the boot seal 140 may be made from a biocompatible silicone to resiliently engage and seal the lead 100 relative to the electrical stimulation device. Other materials may also be used.

Referring again to FIG. 2, the assembled proximal end of the lead may be described. As shown, the electrically conductive connector pin 112 may extend through and may be rotatably disposed in a center bore 150 of a proximal seal 114 and a center bore 118 of a connector insulator 116. The bar portion 164 of the connector pin 112 may be arranged in the center bore 118 of the connector insulator 116. The bar portion 164 may be separated from the inner surface of the center bore 150 by the proximal extension 184 of the connector insulator 116. As such, an inner surface 154 of the connector insulator 116 may provide rotational bearing for the connector pin 112 such that the connector pin 112 may rotate relative to the connector insulator 116 and proximal seal 114. Rotation of the connector pin 112 may drive rotation of the inner coil 120, thereby rotating the helical anchor electrode 108 of the active electrode tip 106 disposed at the distal end 104 of the lead 100. It is appreciated that other suitable rotatable connection structures may be used between the inner coil 120 and the connector pin 112.

The electrically conductive inner conductor or coil 120 may be crimped to the conductor end 162 of the connector pin 112 in conjunction with the pin sleeve 122. The inner insulator tubing 124 may extend over the inner coil 120 and the flared portion 126 thereof may be sleeved onto the distal extension 186 of the connector insulator 116 to abut the inner shoulder 190 of the cascading shoulders and having an outer surface substantially flush with the cylindrical outer surface 127 of the inner shoulder 190. As such, the connector pin 112, the crimp connection, and the inner coil 120 may be substantially fully insulated along its length by the connector insulator 116 and the insulator tubing 124. However, the inner conductor 120 may be exposed via an electrode at the distal end 104 for treatment and the connector pin 112 may be exposed at the proximal end 102 for electrical communication with an electrical stimulation device. The proximal seal 114 may be arranged on the connector insulator 116 and the outwardly projecting ribs 196 may engage a socket on an electrical stimulation device to prevent fluid or other liquid from contacting with the connector pin 112.

The band portion 204 of the ring connector 130 may extend over the flared portion 126 of the insulator tubing 124 and may abut the outer shoulder 188 of the cascading shoulders on the connector insulator 116. As shown, the outer surface of the band portion 204 of the ring connector 130 may be flush with the outer surface 129 of the central body 182 of the connector insulator 116. The outer conductor or outer coil 134 may be arranged to sleevably receive the inner coil 120 and insulator tubing 124. The outer conductor or coil 134 may be crimped to the ring connector 130 by a ring sleeve 136, thereby electrically connecting to the ring connector 130. The boot seal 140 may be positioned over the outer coil 134 and an inwardly protruding rib 143 thereof may engage a slot portion 206 of the ring connector thereby securing the position of the boot seal 140 relative to the ring connector 130. The crimped outer coil 134 and portions of the ring connector 130 may be disposed within a center bore 141 of the boot seal 140. Like the proximal seal 114, the radially projecting ribs 144 of the boot seal 140 may engage a socket on an electrical stimulation device to prevent body fluid or other liquid from contacting the ring connector 130 or otherwise entering the electrical stimulation device.

Accordingly, the connector pin 112 may be electrically connected to the inner coil 120, and the ring connector 130 may be electrically connected to the outer coil 134. In operation of the lead 100, electrical signals may be sent from the proximal end 102 to the distal end 104 via the connector pin 112 and the inner coil 120, and via the ring connector 130 and the outer coil 134. The inner coil 120 may be electrically insulated from the outer coil 134 by the inner insulator tubing 124. The ring connector 130 may be electrically insulated from the inner coil 120 by the inner insulator tubing 124 and the connector insulator 116. The connector pin 112 may be electrically insulated from the ring connector 130 by the proximal seal 114 and the connector insulator 116. The connector pin 112 may be prevented from contacting fluid or other liquid by the sealing ribs 196 of the proximal seal 114. The ring connector 130 may be prevented from being in contact with fluid or other liquid by the sealing ribs 144 of the boot seal 140.

Figure 10A:
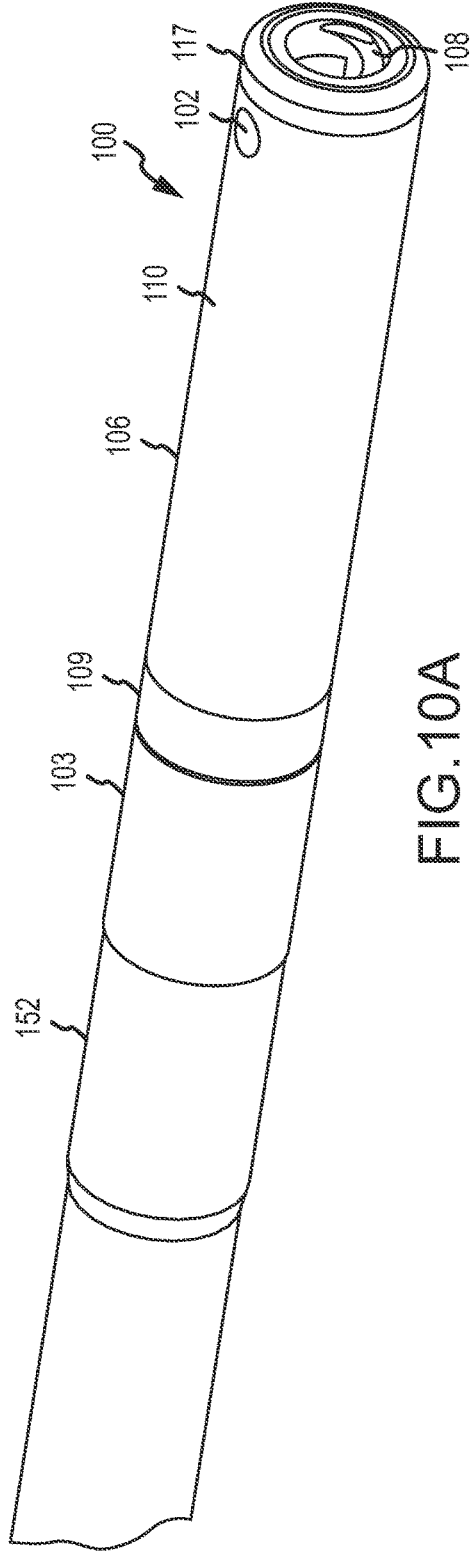
FIGS. 10A and 10B are an isometric view and an isometric cross-sectional view, respectively, of a distal end of the lead of FIG. 1 with an active electrode tip configuration.
Figure 10B:
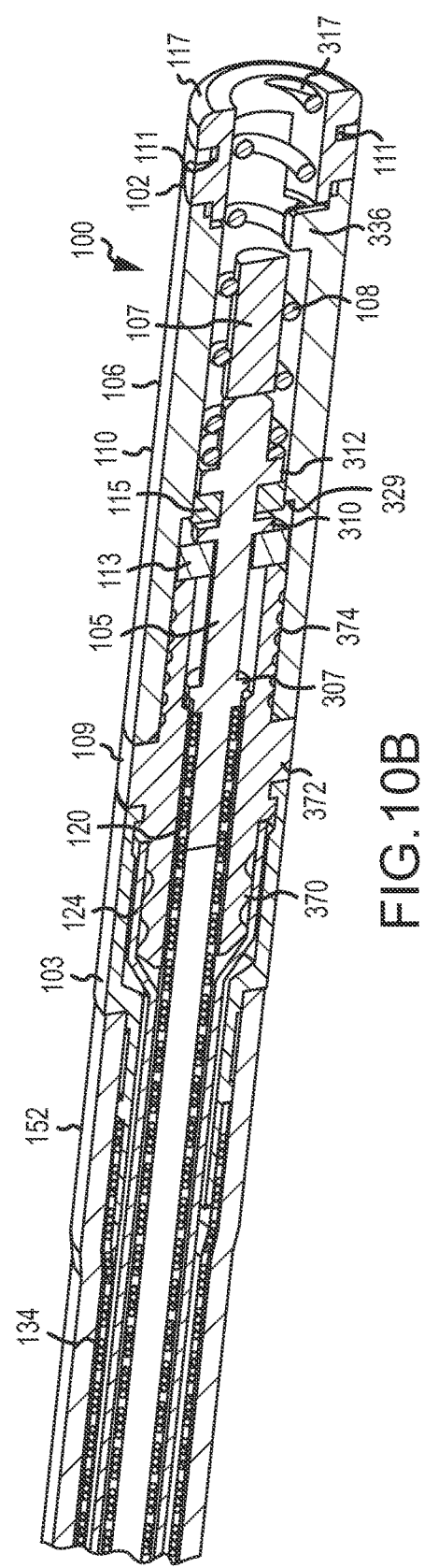
Figure 10C:
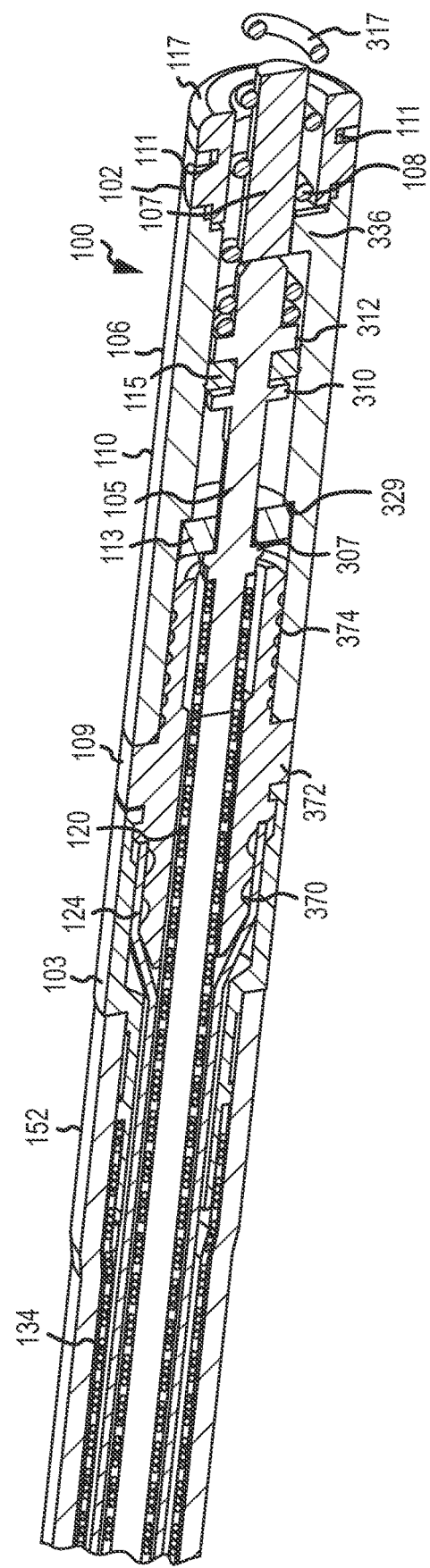
FIG. 10C is an isometric cross-sectional view of the active electrode tip configuration of FIG. 10B with the helical anchor electrode in an extended position.

The active electrode tip 106 at the distal end 104 of the lead 100 is depicted in FIG. 10A and in cross section in FIGS. 10B and 10C. The active electrode tip 106 may be considered to be composed of several primary components:

a ring electrode 103, a tip electrode pin 105, a helical anchor electrode 108, an intermediate connection mount 109, a tip housing 110, and a soft tip plug 117. Additional components may include a marker band 111, a spacer/stopper 113, and a distal seal 115 A proximal end of the ring electrode 103 is electrically and mechanically connected to the distal end of the outer conductor coil 134. The proximal end of the tip electrode pin 105 is electrically and mechanically connected to the distal end of the inner conductor coil 120. The distal end of the tip electrode pin 105 is connected to the proximal end of the helical anchor electrode 108. The intermediate connection mount 109 connects the ring electrode 103 to the tip housing 110 to form an outer surface of the active electrode tip 106. The proximal portion of the tip electrode pin 105 and the helical anchor electrode 108 are substantially encased within the tip housing 110 when the helical anchor electrode 108 is in a retracted state. When the helical anchor electrode 108 is advanced as shown in FIG. 10C and further described below, the distal tip of the helical anchor electrode 108 protrudes beyond the soft tip plug 117 in the distal end of the tip housing 110.

An exemplary embodiment of the tip electrode pin 105 is depicted in greater detail in FIGS. 11A and 11B. The tip electrode pin 105 may be made of a solid conducting material and is generally cylindrical in shape with a number of shaft sections separated by a number of annular flanges. The tip electrode pin 105 may be made, for example, of stainless steel (e.g., 316L), a precious metal (e.g., platinum or iridium), or a metal alloy (e.g., Pt/Ir or MP35N), or another electrically conductive, biocompatible material. At the proximal end, a proximal shaft section 302 of a first diameter is provided. The proximal shaft section 302 is the section of the tip electrode pin 105 that engages the inner conductor coil 120 as will be described in further detail below. The proximal shaft section 302 transitions at a squared shoulder to a larger diameter annular step 303. At the distal edge of the annular step 303, an angled annular wall 305 gradually increases in diameter from the annular step 303 until it intersects a proximal face of a proximal annular flange 307 that functions as a proximal stop feature as further described below. The proximal annular flange 307 is cylindrical and has an outer diameter that is greater than the largest diameter of the angled annular wall 305.

Figure 11:
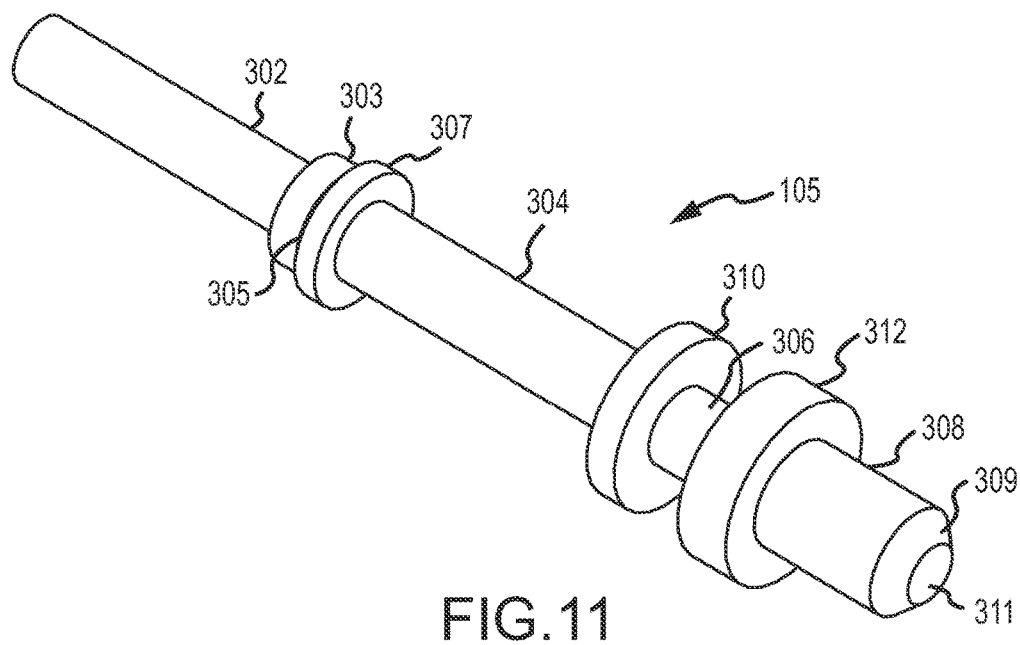
FIG. 11 is an isometric view of a tip electrode pin of the active electrode of FIGS. 10A and 10B.

A medial shaft section 304 may be substantially the same diameter and length as the proximal shaft section 302 extends distally from the proximal annular flange 307 and terminates upon intersecting with a proximal face of a medial annular flange 310 that functions, in part, as a distal stop feature as further described below. The medial annular flange 310 is cylindrical and may have an outer diameter that is greater than the inner diameter of the spacer/stopper ring 113. The medial annular flange 310 may transition distally into a seal shaft section 306 about which a seal ring 115 may be fitted as shown in FIG. 10B and as further described below. The seal shaft section 306 may be of substantially the same diameter as each of the proximal and medial shaft sections 302, 303, but of a substantially shorter length. The seal shaft section 306 may further transition into a cylindrical distal annular flange 312 that is of both a greater outer diameter and a greater longitudinal thickness than the medial annular flange 310. The distal annular flange 312 further transitions into a distal shaft section 308 that is of a greater diameter than the prior shaft sections, but of a smaller diameter than each of the annular flanges. The distal shaft section 308 of the tip electrode pin 105 is the part that directly connects with the proximal end of the helical anchor 108. The distal end of the distal shaft section 308 may have a chamfered edge as shown in FIG. 11 that transitions into a flat tip face 311. The distal shaft section 308 and the distal annular flange 312 may be exposed to the patient's blood when the lead 100 is implanted in vivo.

Figure 12:
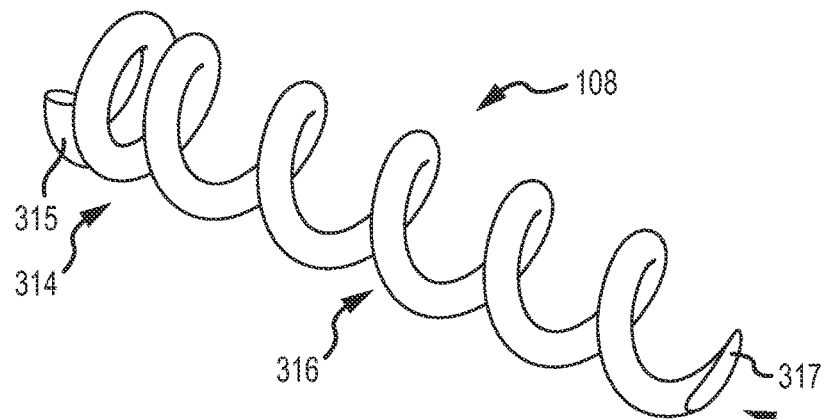
FIG. 12 is an isometric view of a helical anchor electrode of the active electrode tip of FIGS. 10A, and 10B.
Figure 13:
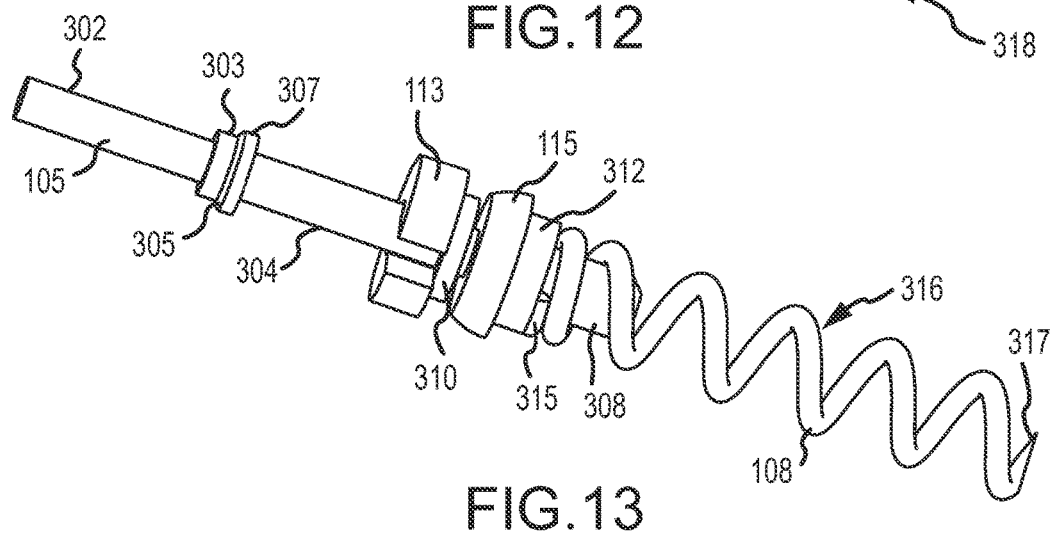
FIG. 13 is an isometric view of helical anchor electrode, a stopper/spacer ring, and a seal ring attached to the tip electrode pin of the active electrode tip of FIGS. 10A and 10B.

An exemplary embodiment of the helical anchor 108 is depicted in isolation in FIG. 12 and in conjunction with the tip electrode pin 105 in FIG. 13. The helical anchor 108 acts as both a conductor and as a fixation structure to anchor the lead 100 into the endocardium within a chamber of the heart. The helical anchor 108 may be made of a solid conducting material, for example, a Platinum/Iridium alloy or another strong, electrically-conductive, biocompatible material formed in a coil shape, with sufficient strength to penetrate into the heart tissue and fix the lead 100 in position for sensing and pacing. The helical anchor 108 may have a proximal connecting section 314, a helical section 316, and a distal end 318. The proximal connecting section 314 may be formed with a close winding 315 at the proximal end where the terminal end of the first winding is adjacent to and in contact with the beginning of the second winding before the windings begin to space apart in a helical shape. The close winding 315 in the proximal connecting section 314 provides for a sufficient surface area contact between the helical anchor 108 and the tip electrode pin 105 to form a strong welded connection as discussed below. The helical section 316 extends distally from the proximal connecting section 314 and the windings in this section take on a helical form. The helical anchor 108 terminates at the distal end 318 in a sharp tip 317 that is able to penetrate and lodge within the endocardial tissue when the helical anchor 108 is rotated like a corkscrew and advances distally out of the active electrode tip 106.

Although not depicted in FIG. 13, the steroid capsule 107 shown in FIGS. 10B and 10C may be placed within the lumen of the helical anchor electrode 108. The steroid capsule 107 may be formed as a cylindrical plug sized to fit snugly within the helical anchor electrode 108. The steroid capsule 107 may be any of a number of steroids (e.g., dexamethasone) or medicaments prepared in a binder for timed release after implantation of the lead 100 in order to promote healing of any trauma caused by placement of the lead 100 or to deliver a desirable drug for efficacy within the heart. The steroid capsule 107 may be adhered within the windings of the helical anchor electrode 108 with a biocompatible adhesive to ensure that the steroid capsule 107 does not dislodge before completely eluting.

Figure 14A:
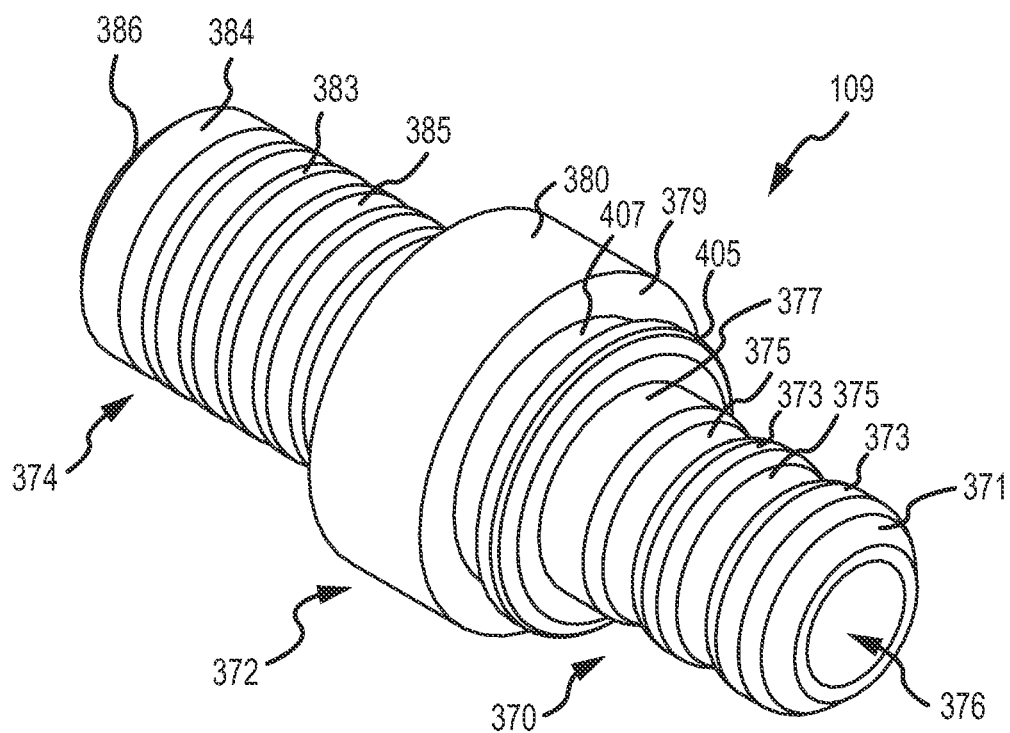
FIGS. 14A and 14B are an isometric view and an isometric cross-sectional view, respectively, of an intermediate connector mount of the active electrode tip of FIGS. 10A and 10B.
Figure 14B:
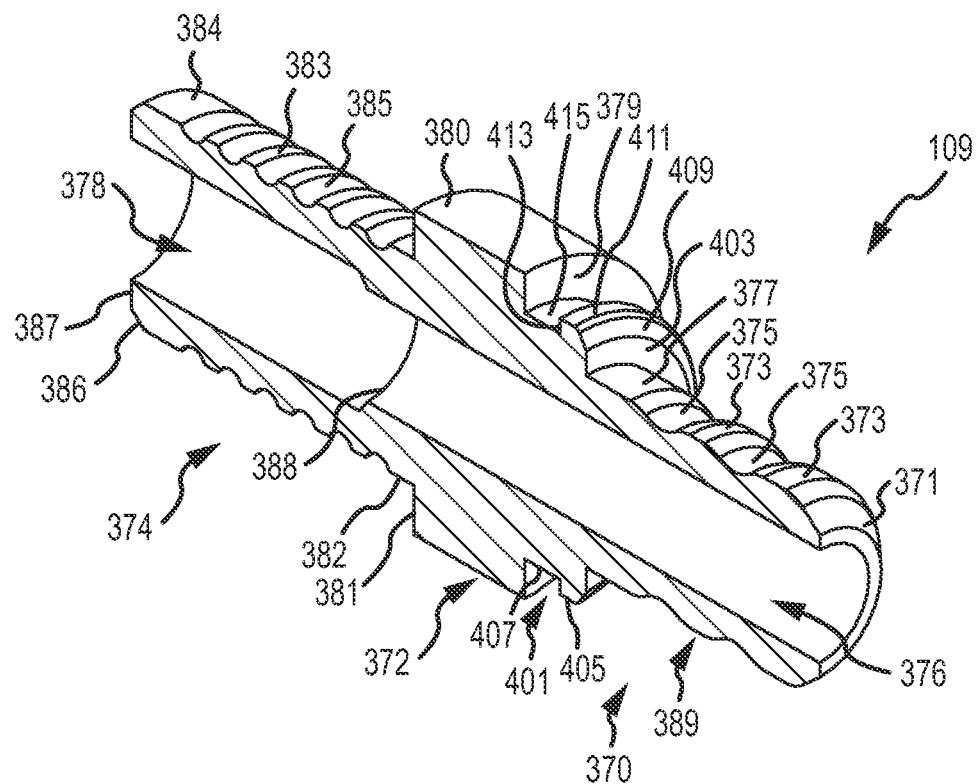

The proximal end of the tip electrode pin 105 is positioned within the intermediate connection mount 109, which is depicted in isolation in FIGS. 14A and 14B. The intermediate connection mount 109 may be understood as a tube-like structure having three primary sections: a proximal fitting 370, a distal fitting 374, and a medial separator 372 located between the proximal and distal fittings 370, 374. The intermediate connection mount 109 defines an axial lumen therethrough from the proximal end to the distal end. The proximal fitting 370 has a proximal section 389 and a distal section 401 located intermediate the proximal section 389 and the medial separator 372. The proximal section 389 is configured to receive the distal end of the insulating tubing 124 surrounding the inner conductor coil 120. The proximal fitting 370 is formed with a tapered slope 371 on the outer diameter thereof increasing in diameter as the tapered slope 371 extends distally. The tapered slope 371 then transitions into a series of alternating arcuate ridges 373 and arcuate channels 375. As shown in FIGS. 14A-14B, the tapered slope 371 transitions into a first, proximal, arcuate ridge 373, which then transitions into a first, proximal arcuate channel 375. The first, proximal arcuate channel 375 transitions into a second, distal arcuate ridge 373, which then transitions into a second, distal arcuate channel 375. The arcuate ridges 373 may be designed to have substantially the same or slightly larger outer diameter as the distal terminus of the tapered slope 371 while the outer diameter of the base of the arcuate channels 375 is less than the outer diameter of the arcuate ridges 373. The distal arcuate channel 375 transitions into a proximal landing 377 that is an annular surface with substantially the same diameter as the diameter of the arcuate ridges 373. The proximal landing 377 interfaces with an abutting surface 403 of the distal section 401 of the proximal fitting 370. The abutting surface 403 may be a substantially square shoulder of the distal section 401.

The distal section 401 of the proximal fitting 370 is intermediate the proximal section 389 and the medial separator 372. The distal section 401 is configured to receive the distal end of the ring electrode 103. The distal section 401 has an annular, radially-extending tab 405 and an annular recess 407 located distally of the tab 405. The tab 405 includes a chamfered proximal surface 409, a substantially square distal shoulder 413, and a substantially cylindrical surface 411 located intermediate the chamfered surface 409 and the square shoulder 413. The interface between the chamfered surface 409 and the cylindrical surface 411 may be arcuate, curved, or rounded. The annular recess 407 is defined by a base wall 415 positioned between the square distal shoulder 413 and an opposing, radially-extending sidewall 379 further described below. The outer diameter of the tab 405 may be greater than the inner diameter of annular recess 407 and less than the outer diameter of the medial separator 372.

The base wall 415 of the annular recess 407 interfaces with a proximal abutting surface 379, which is essentially a square shoulder of the medial separator 372, which is formed as a large cylindrical flange 380 with a flat, annular outer surface. The distal side of the cylindrical flange 380 may also form a square shoulder that provides a distal abutting surface 381 that intersects with a distal landing 382, which is a smooth, annular surface adjacent the cylindrical flange 380. The outer diameter of the distal landing 382 may be substantially the same as the outer diameter of the base wall 415. The distal landing 382 begins the distal fitting 374 of the intermediate connection mount 109. A plurality of alternating shallow channels 385 of arcuate cross section and flat ribs 383 of substantially the same diameter as the distal landing 382 form the majority of the rest of the distal fitting 374 until a tip landing 384 is reached. The tip landing 384 may have a smooth, annular, outer surface and may be of substantially the same outer diameter as each of the distal landing 382 and the flat ribs 383. The tip landing 384 may transition to an annular chamfered tip 386 that further transitions into a flat face 387 at the distal end.

The lumen within the intermediate connection mount 109 may be formed in two parts, a proximal lumen 376 and a distal lumen 378. The proximal lumen 376 may be of smaller inner diameter than the distal lumen 378. A chamfered step 388 within the sidewall of the lumen may be used to transition from the narrower proximal lumen 376 to the wider distal lumen 378.

Figure 15A:
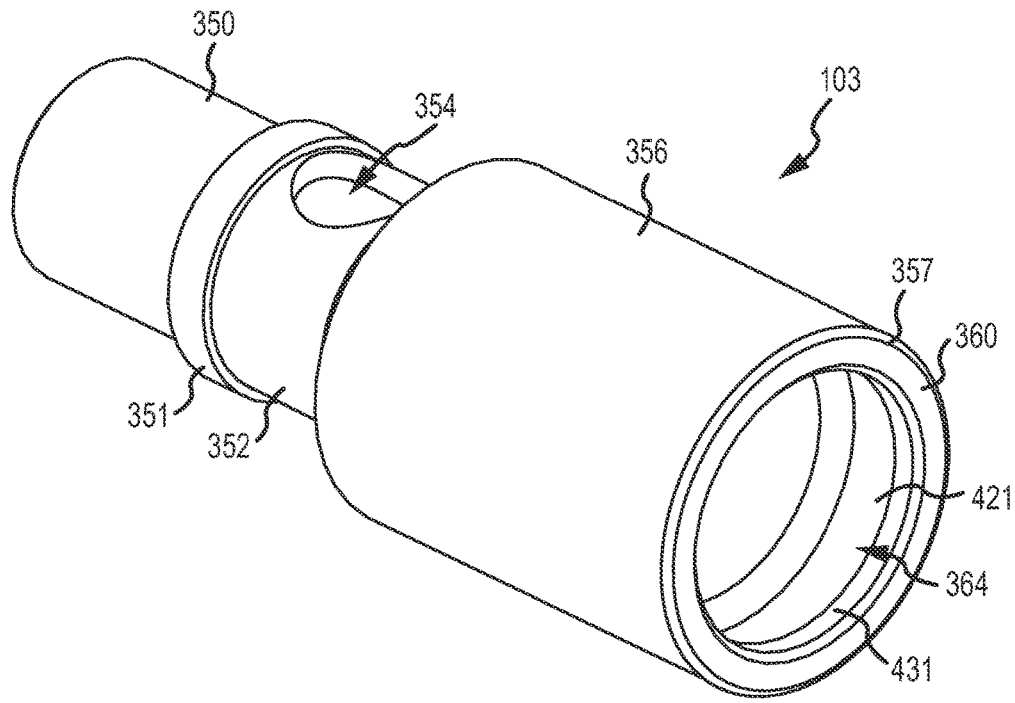
FIGS. 15A and 15B are an isometric view and an isometric cross-sectional view, respectively, of a ring electrode of the active electrode tip of FIGS. 10A and 10B.
Figure 15B:
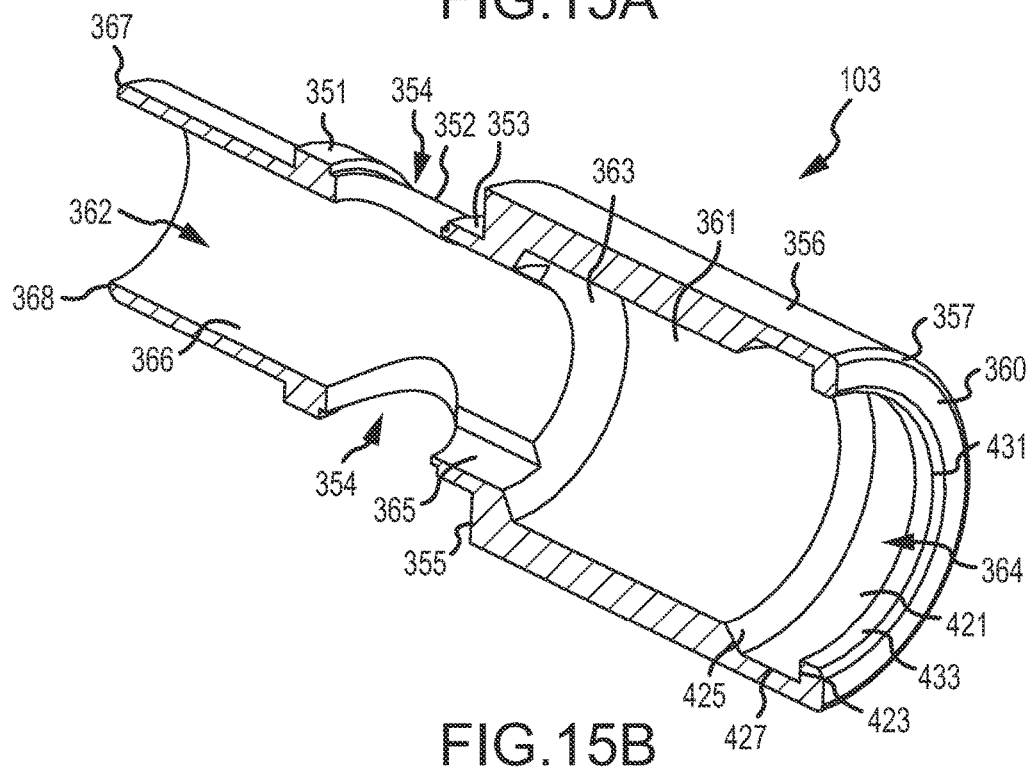

An exemplary embodiment of the ring electrode 103 is depicted in greater detail in FIGS. 15A and 15B. The ring electrode 103 is generally tubular in shape with various cylindrical sections of varying diameter. A smooth, cylindrical proximal sleeve 350 forms the proximal end of the ring electrode 103 and is sized in length and diameter to fit within the distal end of the outer connecter coil 134 and may be laser welded thereto or otherwise securely mechanically attached to form a permanent mechanical and electrical connection. The proximal end of the proximal sleeve 350 may be formed with a proximal chamfered edge 367 that transitions to a proximal flat face 368. An adhesive channel 352 is formed distally adjacent the proximal sleeve 350 and is defined by a proximal curb 351 and a distal curb 353. The proximal curb 351 and the distal curb 353 may be of the same diameter, which may be slightly larger in diameter than the proximal sleeve 350. The adhesive channel 352 may be substantially the same diameter as the proximal sleeve 350. The proximal curb 351 may separate the proximal sleeve from the adhesive channel 352. The diameters of the proximal and distal curbs 351, 353 are selected to be substantially the same as the inner diameter of the outer sheath 152 and the surfaces of the proximal and distal curbs 351, 353 are rough in order to provide a fluid-tight, compression fit with the outer sheath 152. The adhesive channel 352 may define one or more adhesive apertures 354 (two are shown in the exemplary embodiment) in order to introduce a biocompatible adhesive into the channel 352 to bond the ring electrode 103 to the outer sheath 152.

The ring electrode 103 may transition from the adhesive channel 352 via a proximal shoulder 355 adjacent the distal curb 353 to an exposed section 356 of a greater outer diameter. The exposed section 356 is smooth and cylindrical in shape and is not covered or insulated from the patient's blood or tissue. The ring electrode 103 may be made of stainless steel (e.g., 316L), a precious metal (e.g., platinum or iridium), or a metal alloy (e.g., Pt/Ir or MP35N), or another electrically conductive, biocompatible material. The exposed section 356 may be coated with TiN to increase the surface area and thereby achieve a better sensing signal. The distal end of the exposed section 356 transitions with a distal chamfered edge 357 to terminate at a distal flat face 360.

The ring electrode 103 may also define a lumen of two different bore sizes. A proximal bore 362 is sized to be of a slightly larger diameter than the insulating tubing 124 surrounding the inner conductor coil 120 to provide clearance for its passage therethrough. A distal bore 364 is sized to be slightly larger than the proximal section 389 of the proximal fitting 370 of the intermediate connection mount 109 to surround the outer diameter of the insulating tubing 124 sleeved thereon. While the proximal and distal bores 362, 364 have generally smooth walls 366, 361, respectively, the distal end of the distal bore 364 may include an annular groove 421 positioned axially between a distal retaining shoulder 423 and a proximal limit shoulder 425. The distal retaining shoulder 423 may be substantially perpendicular relative to a groove wall 427, and the proximal limit shoulder 425 may be angled or ramped relative to the groove wall 427. The groove 421 is configured to receive the tab 405 of the intermediate connection mount 109.

The distal end of the ring electrode 103 also includes a radially inturned lip 431 located distally of the groove 421. The radially inturned lip 431 has an inner cylindrical surface 433 located intermediate the retaining shoulder 423 and the distal flat face 360. The interface between the inner cylindrical surface 433 and the flat face 360 may be chamfered. The cylindrical surface 433 has an inner diameter that is less than the diameter of the substantially flat groove wall 427 and may be substantially equal to the diameter of the wall 361 of the distal bore 364. The lip 431 may be configured to fig snugly within the annular recess 407 of the intermediate connection mount 109.

A smooth annular wall 361 is formed within the distal bore 364 proximally adjacent the proximal limit shoulder 425. An angled wall 363 is formed proximally adjacent the annular wall 361 to provide the transition to the smaller diameter of the proximal bore 362. A pair of adhesive canals 365 is formed within the proximal bore wall 366 between each of the adhesive apertures 354 and the angled wall 363. The adhesive canals 365 are thus recessed areas within the proximal bore wall 366 that also result in a lower height of the angled wall 363 at its intersection with the proximal bore 362 at the locations of the adhesive canals.

Figure 16:
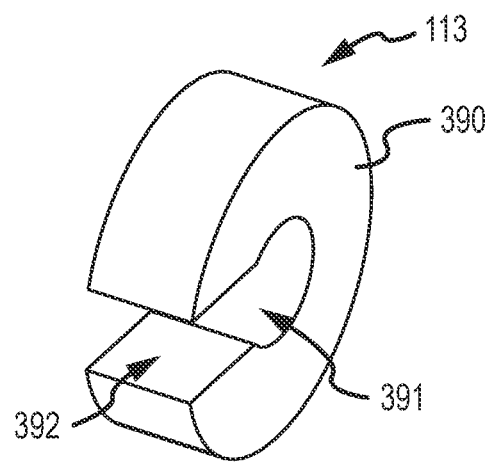
FIG. 16 is an isometric view of a spacer/stopper ring of the active electrode tip of FIGS. 10A, and 10B.

FIG. 16 depicts the spacer/stopper ring 113 that fits around the distal portion of the tip electrode pin 105 beyond the distal end of the intermediate connector mount 109. The spacer/stopper 113 may be formed as a C-shaped body 390 of generally cylindrical form, but that defines a cylindrical aperture 391 aligned along the center axis and a gap 392 in the otherwise annular wall to form the C-shape. The gap 392 allows the spacer/stopper 113 to be easily placed about the medial shaft section 304 of the tip electrode pin 105 adjacent the medial annular flange 310. The spacer/stopper ring 113 may be made of a material that is flexible and resilient enough to allow the gap 392 to be enlarged to fit around the medial shaft section 304 during assembly and then return to its original size and C-shape. The cylindrical aperture 391 is thus substantially the same diameter as the outer diameter of the medial shaft section 304 so that it can easily seat thereon. The gap 392 should be narrower than the outer diameter of the medial shaft section 304 such that once the spacer/stopper 113 is placed on the medial shaft section 304, it will not slide off.

Figure 17A:
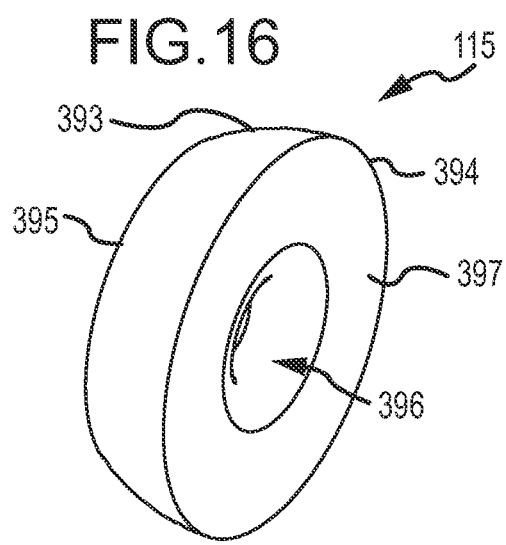
FIGS. 17A and 17B are an isometric view and an isometric cross-sectional view, respectively, of a distal seal ring of the active electrode tip of FIGS. 10A and 10B.
Figure 17B:
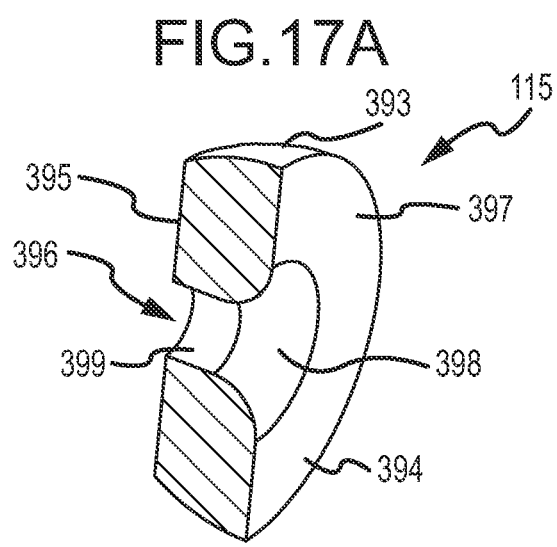

FIGS. 17A and 17B depict an exemplary embodiment of the seal ring 115 in isolation. The seal ring 115 is formed as a generally annular body 394 defining a lumen axially therethrough. The seal ring 115 may be made of an elastomeric material that is flexible and resilient enough to fit over the distal shaft section and the distal annular flange 312 of the tip electrode pin 105 such that the seal ring 115 can seat about the seal shaft section 306 on the tip electrode pin 105. The annular body 394 has a flat proximal face 395 and a flat distal face 397 and a curved radial wall 393. The outer diameter at the edge of the distal face 397 and the radial wall 393 is larger than the outer diameter at the edge of the proximal face 395 and the radial wall 393. Thus, the outer diameter of the annular body 394 decreases from the distal face 397 to the proximal face 395 following the curve of the radial wall 393. The distal face 397 also transitions from a flat surface to a radius entrance 398 to the lumen. The radius entrance 398 transitions to a cylindrical section 399 part way through the lumen and maintains the cylindrical form until the lumen exits the proximal face 395

Figures 18A, 18B:
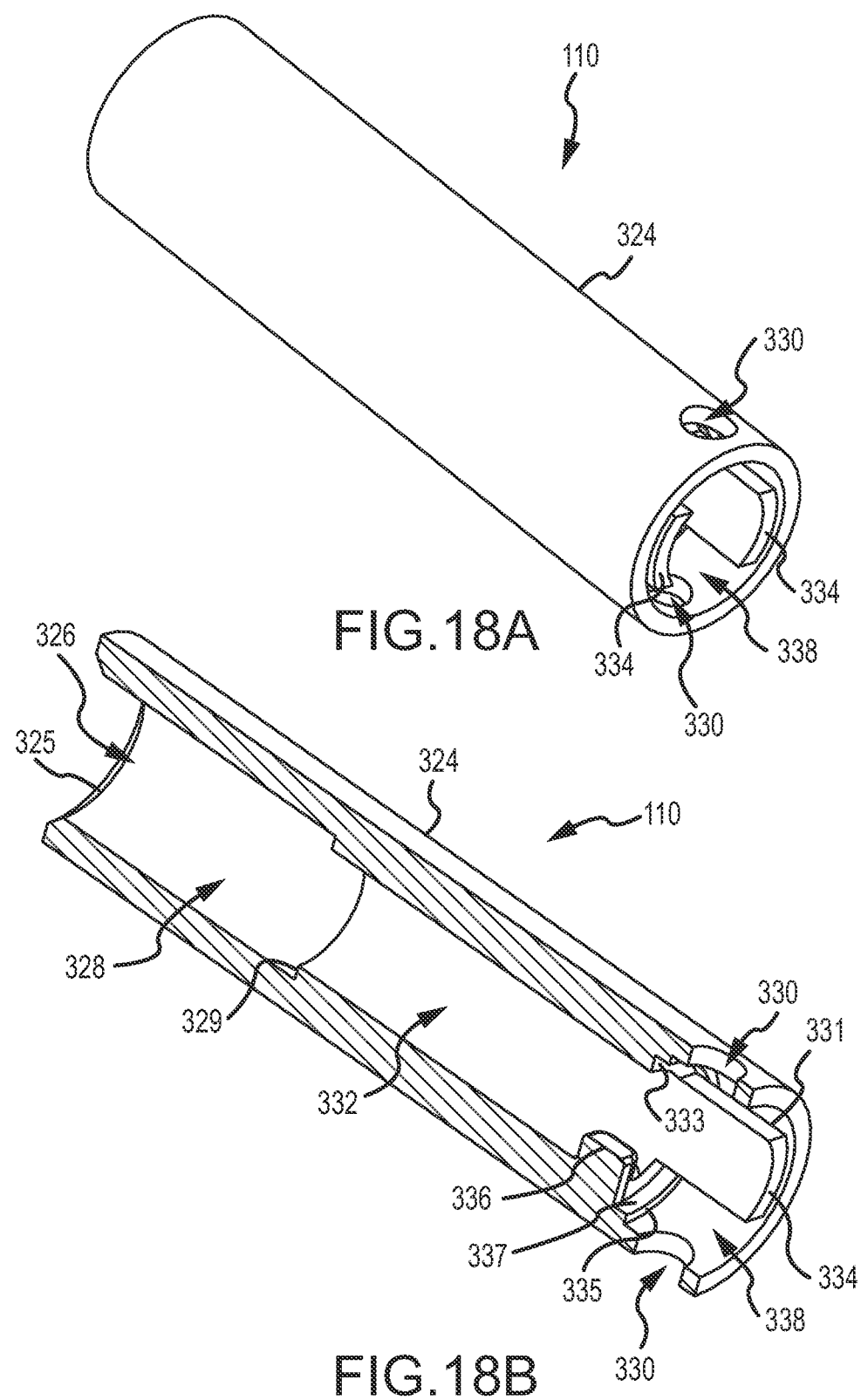
FIGS. 18A and 18B are an isometric view and an isometric cross-sectional view, respectively, of a tip housing of the active electrode tip of FIGS. 10A and 10B.

An exemplary embodiment of the tip housing 110 is depicted in greater detail in FIGS. 18A and 18B. The tip housing 110 may be generally cylindrical in shape with a long tubular sheath 324 of a substantially constant outer diameter along its length. The tubular sheath 324 may define an axial lumen therethrough from the proximal end to the distal end. Two retention apertures 330 may be formed through the wall of the tubular sheath 324 adjacent the distal end and at symmetrically opposite locations thereon. The tip housing 110 may be formed of a resilient biocompatible material (e.g., polyether ether ketone (PEEK) or polysulfone) in order to be fitted over the intermediate connection mount and retained thereon.

At a proximal end, the lumen may define a sleeve bore 328 of relatively larger diameter with respect to the rest of the lumen 326 that is sized in both diameter and length to sleeve over and create a fluid-tight connection with the distal fitting 374 of the intermediate connection mount 109. The proximal end of the tubular sheath 324 may provide a chamfered entrance 325 to the sleeve bore 328. The sleeve bore 328 transitions at a squared sleeve shoulder 329 to a relatively long middle bore 332 of a narrower inner diameter that is sized to extend primarily over the helical section 316 of the helical anchor electrode 108. The middle bore 332 also acts as a sealing section to form a fluid-tight seal with the seal ring 115 as further described below. An anchor guide 336 protrudes from a wall of the middle bore 332 at the distal end thereof and extends radially inward into the lumen 326. The anchor guide 336 may be sized to fit between adjacent windings of the helical anchor electrode 108 and extend a distance slightly greater than a diameter (thickness) of the windings of the helical anchor electrode 108. As shown in the exemplary embodiment, the anchor guide 336 is aligned longitudinally with one of the retention apertures 330; however, it may be located at any position about the circumference of the middle bore 332.

The middle bore 332 may transition into a tip bore 338 of a larger inner diameter via a stepped structure including a squared shoulder 333 that increases the lumen diameter slightly to an annular shelf 337, which further transitions to a shelf shoulder 335 that ultimately extends the lumen radially to the diameter of the tip bore 338. The retention apertures 330 described above are positioned within the tip bore 338 in the lumen 326. Additionally, a pair of guide walls 334 extend into the tip bore 338 as extensions of the middle bore 332. The guide walls 334 are arcuate in form, are symmetrically opposed from each other within the tip bore 338, may be generally rectangular in projection of their perimeter boundaries, and a separation distance between opposing points on the guide walls 334 is the same as the diameter of the middle bore 332. The guide walls 334 are spaced apart from the wall of the tip bore 338 by respective retention posts 331 centered on the outer sides of the guide walls 334. The retention posts 331 connect the guide walls 334 to the wall defining the tip bore 338 and define the separation distance between the two. The retention posts 331 may be cylindrical in shape and spaced apart from the annular shelf 337 such that there is void space on all sides of the retention posts 331 between the guide walls 334 and the wall defining the tip bore 338. The retention posts 331 may be formed on the inner wall of the tubular sheath 324 defining the tip bore 338 symmetrically opposite each other and equidistant from the retention apertures 330 such that there is a 90° separation between adjacent retention apertures 330 and retention posts 331.

Figure 19:
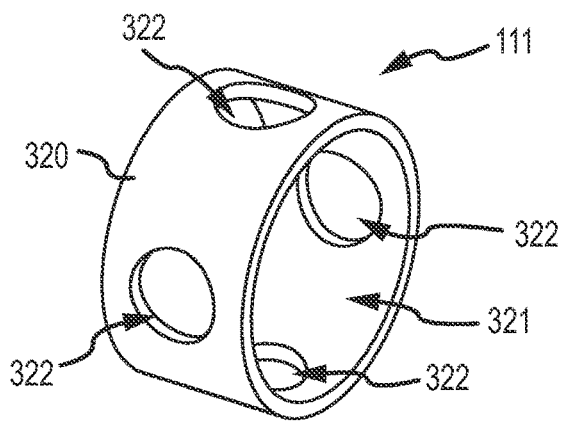
FIG. 19 is a view showing an exemplary embodiment of a marker band formed of a radiopaque material.

An exemplary embodiment of a marker band 111 is shown in isolation in FIG. 19. The marker band 111 may be formed of a radiopaque material, e.g., a Pt/Ir alloy or a thermoplastic compound suitable for injection-molding and having an opacity to X-rays more than sufficient to guarantee shielding comparable to that of a metal. The marker band 111 provides a mark for a physician to identify under fluoroscopy the location of the distal end 104 of the active electrode tip 106 and allows the physician to determine whether the helical anchor electrode 108 is at retracted position or extension position or in between by comparing the position of the helical anchor electrode 108 to the marker band 111. The marker band 111 may be formed as an annular wall 320 defining a cylindrical lumen 312. The outer diameter of the annular wall 320 may be congruent with the inner diameter of the tip bore 338 of the tip housing 110 within which the marker band 111 resides and is formed as described further below. The thickness of the annular wall 320 is such that the diameter of the cylindrical lumen 321 is congruent with the diameter of the annular shelf 337. The annular wall 320 further defines four sidewall retention holes 322 that are spaced 90° apart for alignment with respective ones of the retention posts 331 and retention apertures 330 on the tip housing 110.

Figure 20A:
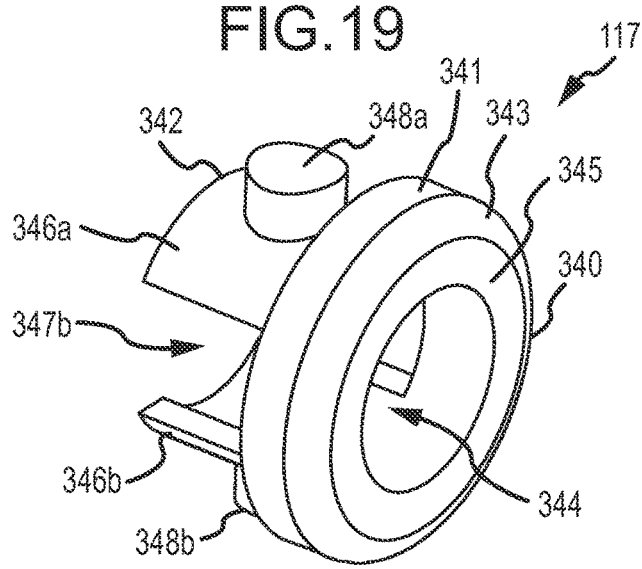
FIGS. 20A and 20B are a distal isometric view and a proximal isometric view, respectively, of a soft tip plug of the active electrode tip of FIGS. 10A and 10B.
Figure 20B:
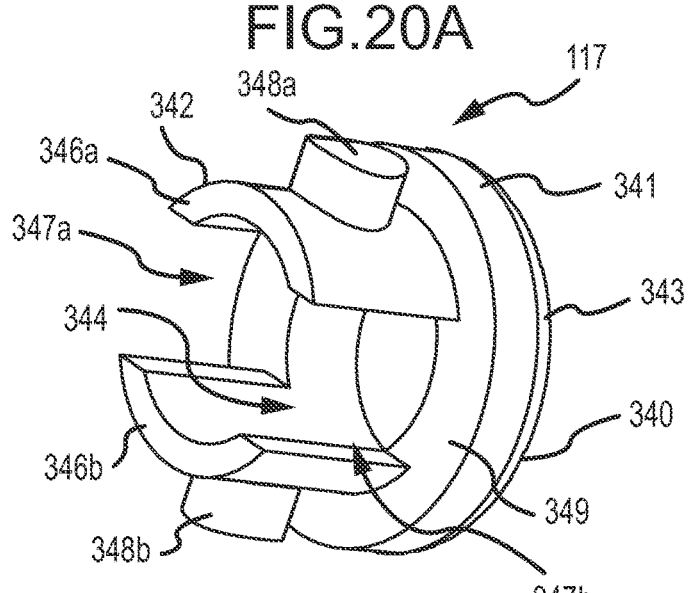

FIGS. 20A and 20B depict an exemplary embodiment of the soft tip plug 117, which fits within and connects to the tip bore 338 of the tip housing 110. The soft tip plug 117 may be formed of a molded, biocompatible, elastomeric material designed to minimize trauma to vasculature and tissue, including lead perforation, as the lead 100 is positioned for implantation. In some embodiments, the soft tip plug 117 may be coated with a steroid (e.g., dexamethasone) for relieving inflammation at the implant location or with other medicinal agents. The soft tip plug 117 may be composed of an exposed section 340 and a retention section 342 extending proximally from the exposed section 340. The exposed section 340 may be formed as a ring defining a tip lumen 344 and defined by a smooth annular edge 341, a flat proximal face 349, a flat distal face 345, and a chamfered face 343 transitioning between the annular edge 341 and the distal face 345.

The retention section 342 of the soft tip plug 117 may be primarily composed of a pair of arcuate walls 346 a/b that extend proximally from the proximal face 349 of the exposed section 340. The arcuate walls 346 a/be may be arranged symmetrically opposite each other about the tip lumen 344 and are separated at lateral edges by a pair of gaps 347 a/b. The tip lumen 344 may be of constant diameter through each of the exposed section 340 and the retention section 342. The outer diameter of the arcuate walls 346 a/b may be congruent with the inner diameter of the tip bore 338 such that the arcuate walls 346 a/b may be received within the tip bore 338. The diameter of the annular edge 341 may be congruent with the outer diameter of the tip housing 110 such that the exposed section 340 smoothly transitions into the tip housing 110. A pair of retention plugs 348 a/b may be formed on the outer surfaces of respective annular walls 346 a/b and extend radially therefrom to a height congruent with the annular edge 341. The retention plugs 348 a/b are configured to fit within the retention apertures 330 in the tip housing 110 to retain the soft tip plug 117 within the distal bore 330 of the tip housing 110.

Since the lead 100 is bipolar, two electrical connections must be made between the proximal end 102 and the distal end 104. The inner conductor coil 120 and the outer conductor coil 134 provide the electrical connection between the proximal end 102 and distal end 104 of the lead 100. As shown in FIG. 10B, the inner conductor coil 120 fits over the proximal shaft section 302 of the tip electrode pin 105 to abut the annular step 303 and is laser welded circumferentially to the proximal shaft section. On the distal end of the tip electrode pin 105, the helical anchor electrode 108 is place upon and also laser welded (e.g., by spot welding) to the distal shaft section 108 to complete a connection with the inner conductor coli 120 and provide an electrical impulse current to the heart.

The proximal shaft section 302 of the tip electrode pin 105 and corresponding connection with the inner conductor coil 120 reside within the proximal lumen 376 of the intermediate connection mount 109. The diameter of the proximal lumen 376 is larger than the diameter of the inner conductor coil 120 when sleeved over the proximal shaft section 302, thereby allowing the tip electrode pin 105 and attached inner conductor coil 120 to freely rotate within the proximal lumen of the intermediate connection mount 109. The angled annular wall 305 of the tip electrode pin 105 interfaces with the chamfered step 388 within the intermediate connection mount 109 to provide an axial alignment interface and opposing bearing surfaces to allow for rotation of the inner conductor coil 120 and the tip electrode pin 105 within the intermediate connection mount 109. The insulating tubing 124 (e.g., silicon) covering substantially the entire length of inner conductor coil 120 from the proximal end 102 of the lead 100 through the outer sheath 152 may be expanded and flared upon reaching the tapered end 371 of the intermediate connection mount 109 to sleeve over the proximal fitting 370 until it abuts the proximal abutting surface 379. The elastic properties of the insulating tubing 124 cause it to radially shrink and compress from the expanded form around the proximal fitting 370. A fluid-tight, compression fit is thus formed between the insulating tubing 124 and the proximal fitting 370 of the intermediate connection mount 109. Electrical insulation is thus provided between the inner conductor coil 120 and the outer conductor coil 134 along the entire length of the lead 100.

The outer conductor coil 134 is designed to sleeve over the proximal sleeve 350 of the ring electrode 103 with mild radial expansion until it abuts the proximal curb 351 and is then laser welded circumferentially to the proximal sleeve, whereby electrical impulses from the heart can be sensed by the ring electrode 103 and transmitted through the lead 100 to a base unit for monitoring and processing. The diameter of the proximal bore 366 of the proximal sleeve 350 is larger than the diameter of the inner conductor coil 120 and the insulating tubing 124, thereby allowing the insulating tubing 124 and inner conductor coil 120 to freely fit within and move proximally and distally as the helical anchor electrode 108 is extended and retracted into and out of the distal tip 106.

The exposed section of the ring electrode 103 is sleeved over the distal end of insulating tubing 124, which is stretched over the proximal section 389 of the proximal fitting 370 of the intermediate connection mount 109. The proximal bore wall 366 of the ring electrode 103 may be bonded to the insulating tubing 124 with medical adhesive, which may be applied through the adhesive apertures 354. The outer sheath 152 is sleeved over the distal end of the outer conductor coil 134 and further over the proximal and distal curbs 351, 353 of the ring electrode 103 until it abuts the outer shoulder. Medical adhesive within the adhesive channel between the proximal and distal curbs 351, 353 bonds the outer sheath 152 to the proximal end of the ring electrode 103.

With reference to FIGS. 10B and 10C, 14A, 14B, 15A, and 15B, the ring electrode 103 and the intermediate connection mount 109 are designed to snap together to axially secure the ring electrode 103 and the intermediate connection mount 109. The snap engagement may improve the mechanical strength of the connection joint between the ring electrode 103 and the intermediate connection mount 109. Additionally or alternatively, the snap engagement may eliminate the use of medical adhesive or other bio-compatible glue for connecting the ring electrode 103 and the intermediate connection mount 109. Optionally, in some implementations, medical adhesive may be applied through the adhesive apertures 354 and may travel within the adhesive canals 365 in the ring electrode 103 to flow along the outer surface of the insulating tubing 124 and within the distal bore 364 to further enhance the joint strength between the ring electrode 103, the insulator tubing 124, and/or the intermediate connection mount 109.

With continued reference to FIGS. 10B and 10C, 14A, 14B, 15A, and 15B, the inturned lip 431 of the ring electrode 103 is seated in the recess 407 of the intermediate connection mount 109, and the tab 405 of the intermediate connection mount 109 is seated in the groove 421 of the ring electrode 103. The width of the lip 431 may be congruent with the width of the annular recess 407 to substantially prevent axial displacement of the lip 431 within the recess 407. That is, the distal face 360 of the ring electrode 103 may abut the proximal abutting surface 379 of the medial separator 372 of the intermediate connection mount 109, and the distal retaining shoulder 423 of the inturned lip 421 may abut the square shoulder 413 of the tab 405 to axially interlock the ring electrode 103 and the intermediate connection mount 109. The height of the lip 431 may be congruent with a depth of the annular recess 407 to maintain a flush transition between the outer surfaces of the ring electrode 103 and the intermediate connection mount 109. That is, the distance between the cylindrical surface 433 and the exposed section 356 of the ring electrode 103 may be approximately equal to the distance between the base wall 415 of the annular recess 407 and the outer surface of the cylindrical flange 380 of the intermediate connection mount 109.

During connection of the ring electrode 103 and the intermediate connection mount 109, the chamfered interface between the face 360 and the cylindrical surface 433 of the ring electrode 103 contacts the chamfered proximal surface 409 of the tab 405 of the intermediate connection mount 109. Depending upon the material properties of the ring electrode 103 and the intermediate connection mount 109, the lip 431, the tab 405, or both may resiliently deform to permit the lip 431 to pass axially by the tab 405. Once the lip 431 clears the tab 405, the lip 431, the tab 405, or both elastically return to their non-deformed states to axially interconnect the ring electrode 103 and the intermediate connection mount 109. In some implementations, the lip 431 may frictionally engage at least one surface of the annular recess 407, the tab 405 may frictionally engage at least one surface of the groove 421, or both, to constrict rotation of the ring electrode 103 relative to the intermediate connection mount 109. In some implementations, rotation of the ring electrode 103 relative to the intermediate connection mount 109 is restricted by adding bond material, such as silicone, epoxy, or other suitable materials. In some implementations, the ring electrode 103 and the intermediate connection mount 109 may be disconnected from each other without permanently damaging either component.

The mechanical strength of the snap or interference fit between the ring electrode 103 and the intermediate connection mount 109 depends upon the design of the locking feature of the components. For example, the material strength, elasticity, diameter, and thickness of the locking features (i.e., the lip 431 and the tab 405) affect the mechanical snap-fit connection strength. The tab 405 of the intermediate connection mount 109 shown in FIGS. 14A and 14B extends continuously around the periphery of the mount 109 to increase the strength of the snap engagement connection. The tab 405 also includes a chamfered proximal surface 409 to reduce an insertion force and a square distal shoulder 413 to increase a disconnection force. Similarly, the lip 431 of the ring electrode 103 extends continuously around the inner periphery of the electrode 103 to increase the strength of the snap-fit connection. The lip 431 also includes a chamfered distal surface for reducing an insertion force and a square proximal surface 423 to matingly engage the square distal shoulder 413 of the intermediate connection mount 109 and increase a disconnection force.

Figure 14C:
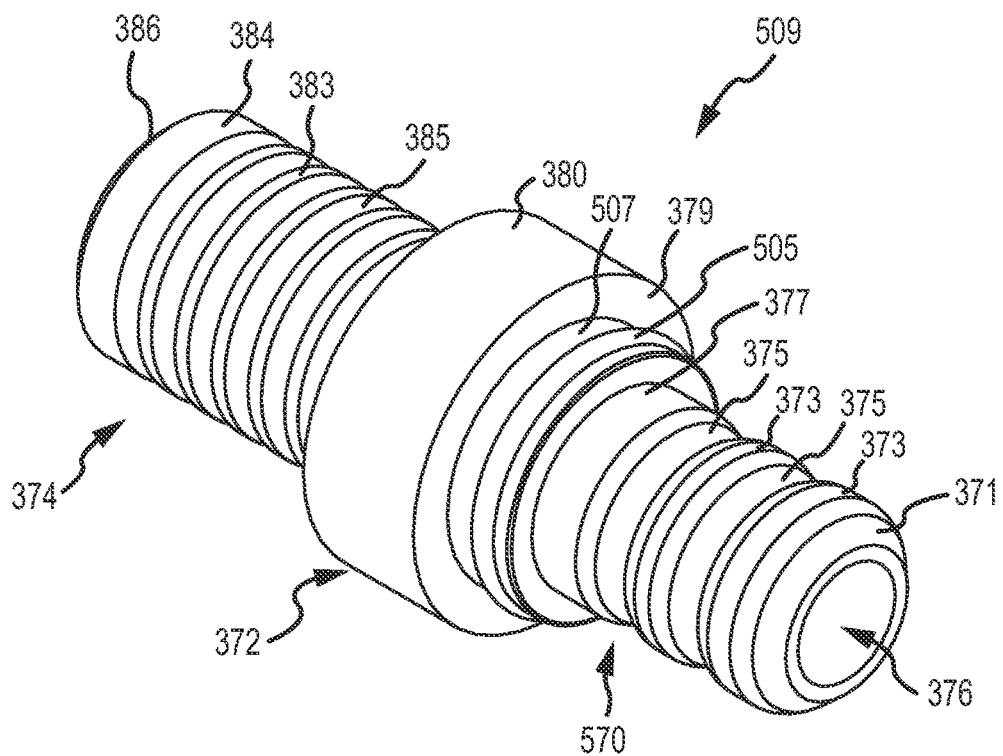
FIGS. 14C and 14D are an isometric view and an isometric cross-sectional view, respectively, of an alternative intermediate connector mount.
Figure 14D:
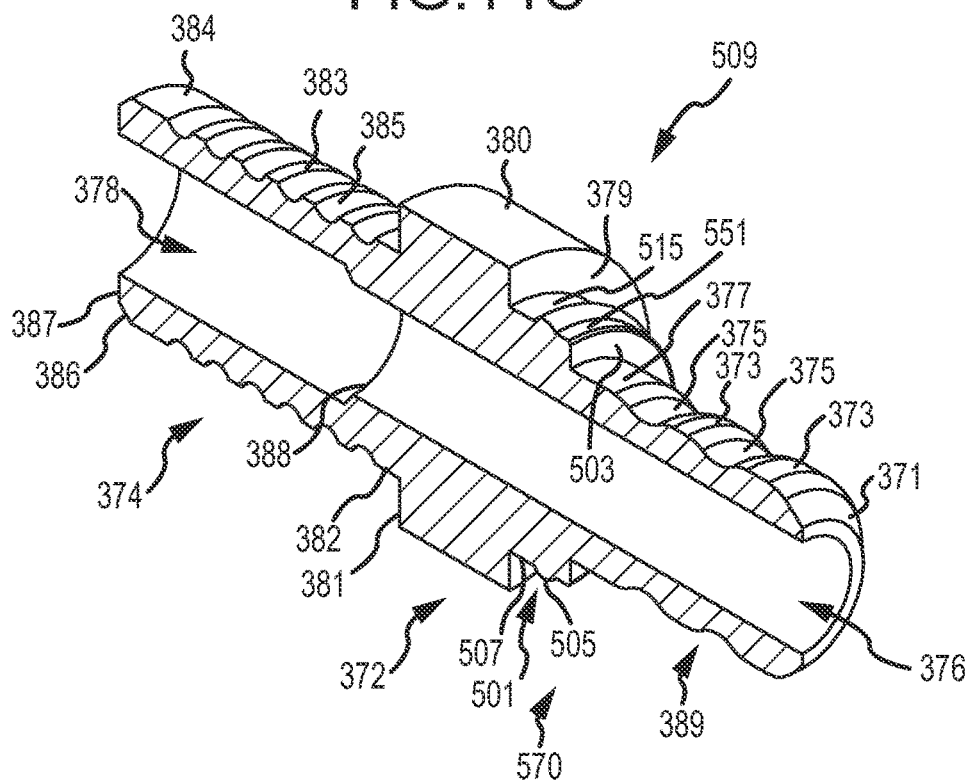

With reference to FIGS. 14C and 14D, an alternative intermediate connection mount 509 is provided. The connection mount 509 generally has the same features as the connection mount 109 depicted in FIGS. 14A and 14B except the distal section 501 is modified to reduce the strength of the snap interlock connection. Similar to the tab 405 depicted in FIGS. 14A and 14B, the tab 505 depicted in FIGS. 14C and 14D is annular and continuous. That is, the tab 505 protrudes radially outward from the base wall 515 of the groove 507 and forms a continuous ring around the distal section 501 of the intermediate connection mount 509. However, relative to the tab 405, the tab 505 has a smaller height, and thus a smaller outer diameter, thereby reducing the amount of mechanical interference between the tab 505 and the lip 431 of the ring electrode 103 during connection and/or disconnection of the components. As shown in FIGS. 14C and 14D, the tab 505 has an arcuate outer surface, which may be approximately semicircular in cross-section, that may further reduce the amount of mechanical interference between the tab 505 and the lip 431 of the ring electrode 103 during connection and/or disconnection of the components. The distal section 501 also includes an annular landing 551 disposed between the tab 505 and the abutting surface 503. The annular landing 551 is substantially cylindrical in shape and may have approximately the same diameter as the recess 507, which may generally correspond to the diameter of the lip 431 of the ring electrode 103. Thus, the annular landing 551 may function as a temporary seat for the lip 431 and ensure the lip 431 is coaxial with the tab 505 upon engagement of the lip 431 and the tab 505.

Figure 14E:
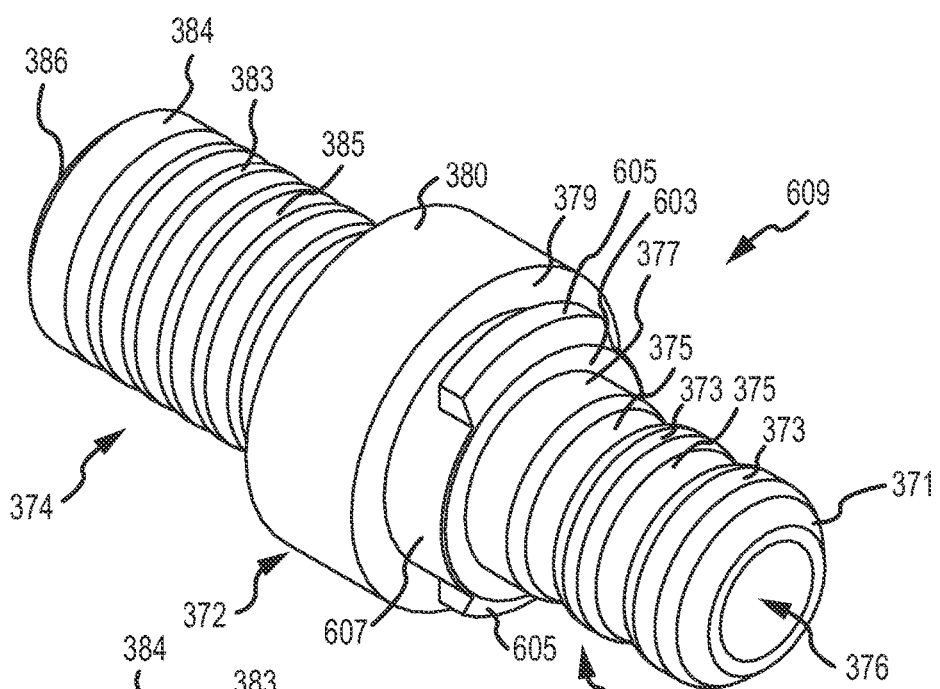
FIGS. 14E, 14F, and 14G are an isometric view, an isometric cross-sectional view, and a proximal, elevation side view, respectively, of another alternative intermediate connector mount.
Figure 14F:
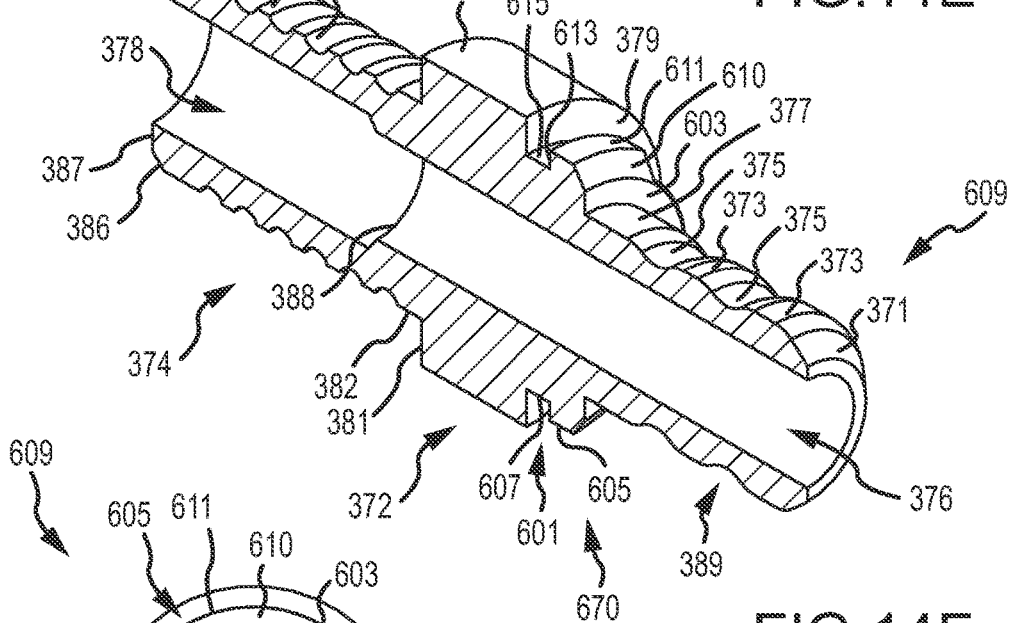
Figure 14G:
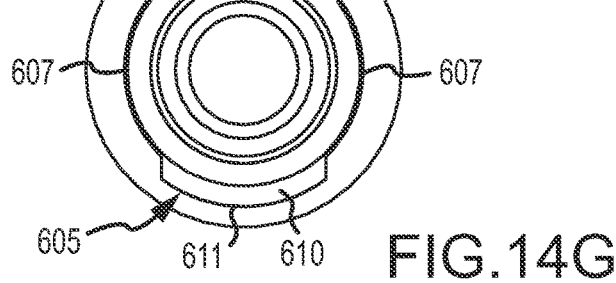

With reference to FIGS. 14E through 14G, another alternative intermediate connection mount 609 is provided. The connection mount 609 generally has the same features as the connection mount 109 depicted in FIGS. 14A and 14B except the distal section 601 is modified to reduce the strength of the snap interlock connection. The tabs 605 depicted in FIGS. 14E through 14G each have substantially the same cross-sectional shape as the tab 405 depicted in FIGS. 14A and 14B. That is, the tabs 605 each have a chamfered proximal surface 610 (although the slope of the chamfered proximal surface 610 is longer than the chamfered surface 409 of the tab 405), a substantially square distal shoulder 613, and a substantially cylindrical surface 611 located intermediate the chamfered surface 610 and the square shoulder 613. However, in contrast to the continuous tab 405 of FIGS. 14A and 14B, in FIGS. 14E through 14G a plurality of discontinuous tabs 605 are disposed around the periphery of the distal section 601. In particular, two diametrically opposed tabs 605 protrude outwardly from the base wall 615 of the recess 607. The tabs 605 collectively extend around about one-half of the periphery of the distal section 601, although in other implementations the tabs 605 may extend around a majority or a minority of the periphery of the distal section 601. Since the tabs 605 are discontinuous and spaced apart from each other, voids are formed between the tabs 605. The voids reduce the amount of material that engages the lip 431 of the ring electrode 103, thereby reducing the mechanical strength of the snap-fit connection relative to the snap lock features illustrated in FIGS. 14A and 14B.

Figure 14H:
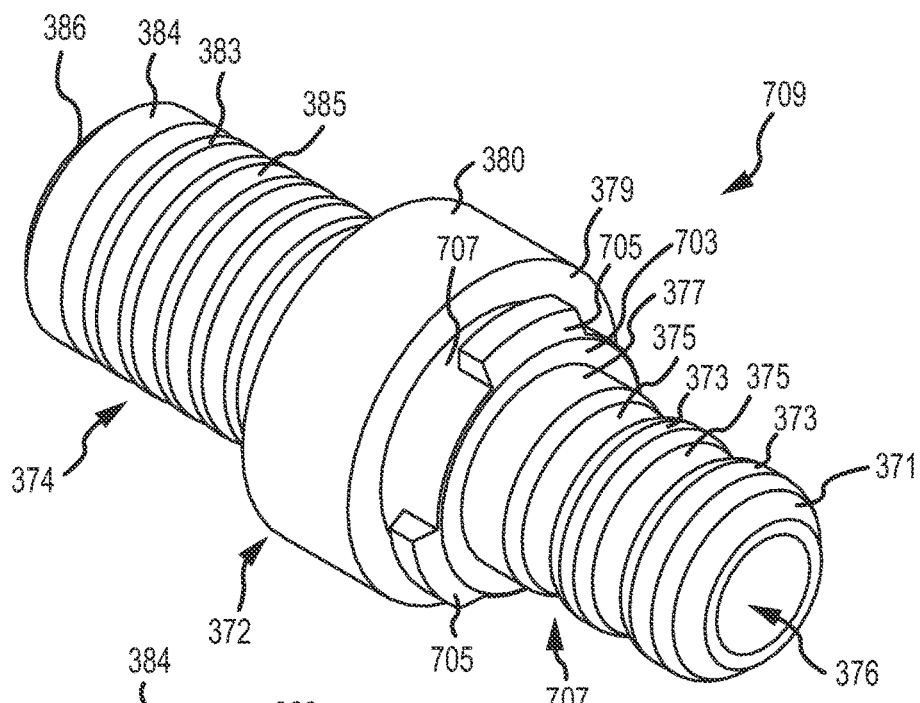
FIGS. 14H, 14I, and 14J are an isometric view, an isometric cross-sectional view, and a proximal, elevation side view, respectively, of yet another alternative intermediate connector mount.
Figure 14I:
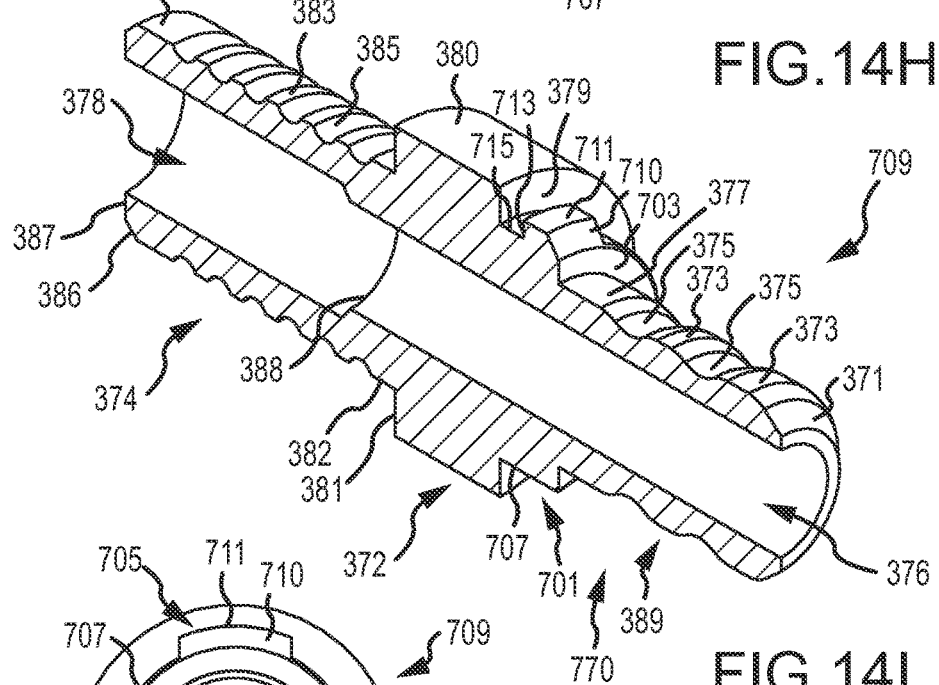
Figure 14J:
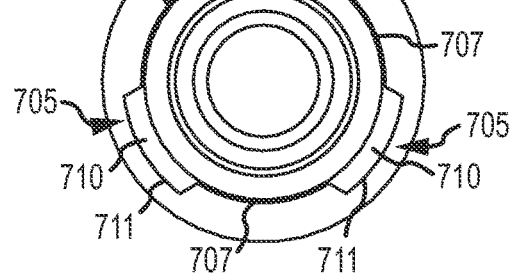

With reference to FIGS. 14H through 14J, another alternative intermediate connection mount 709 is provided. The connection mount 709 generally has the same features as the connection mount 109 depicted in FIGS. 14A and 14B except the distal section 601 is modified to reduce the strength of the snap lock mechanism. The tabs 705 depicted in FIGS. 14H through 14J each have substantially the same cross-sectional shape as the tab 405 depicted in FIGS. 14A and 14B. That is, the tabs 705 each have a chamfered proximal surface 710 (although the slope of the chamfered proximal surface 710 is longer than the chamfered surface 409 of the tab 405), a substantially square distal shoulder 713, and a substantially cylindrical surface 711 located intermediate the chamfered surface 710 and the square shoulder 713. However, in contrast to the continuous tab 405 of FIGS. 14A and 14B, in FIGS. 14H through 14J a plurality of discontinuous tabs 705 are located around the periphery of the distal section 701. In particular, three tabs 605 are evenly spaced about the periphery of the connection mount 709 and protrude outwardly from the base wall 715 of the recess 707. The tabs 705 collectively extend around about one-half of the periphery of the distal section 701, although in other implementations the tabs 705 may extend around a majority or a minority of the periphery of the distal section 701. Similar to the example depicted in FIGS. 14E through 14G, voids are formed between the tabs 705 and reduce the amount of material that contacts the lip 431 of the ring electrode during connection and disconnection of the connection mount 709 and the ring electrode 103.

Figure 14K:
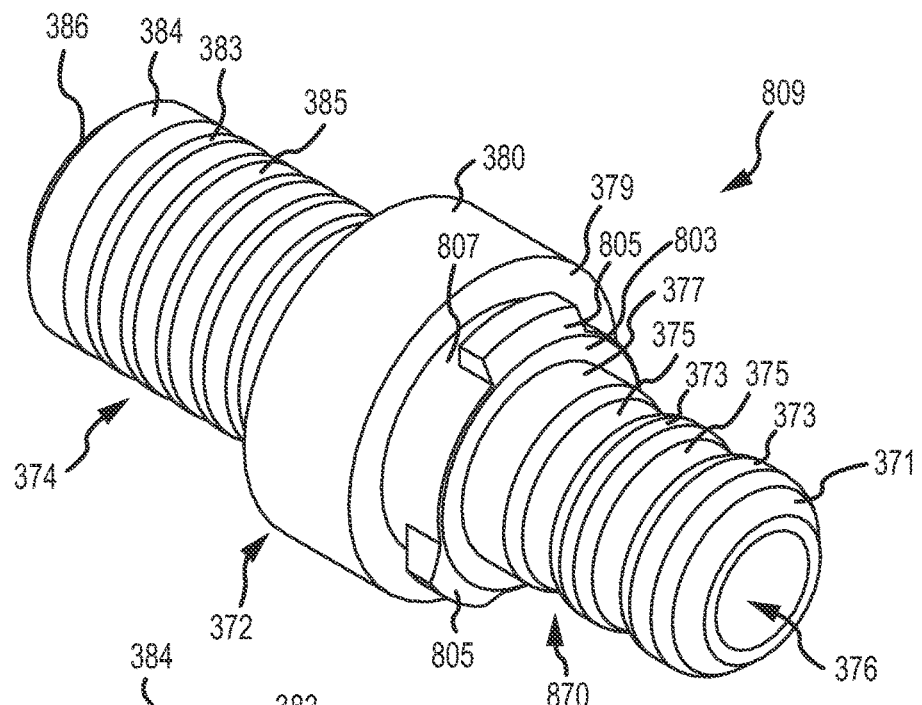
FIGS. 14K, 14L, and 14M are an isometric view, an isometric cross-sectional view, and a proximal, elevation side view, respectively, of a further alternative intermediate connector mount.
Figure 14L:
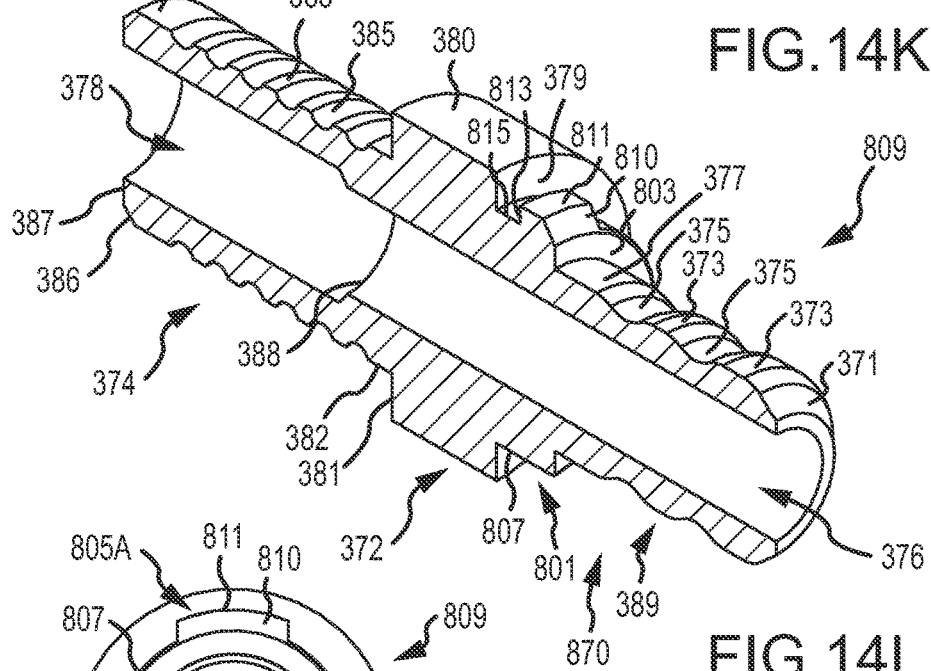
Figure 14M:
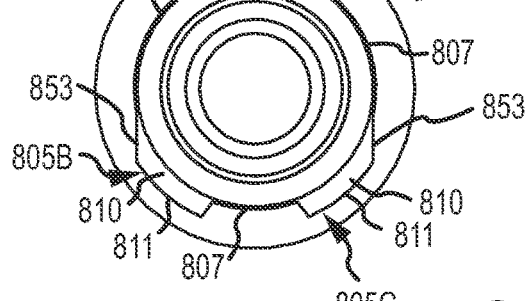

With reference to FIGS. 14K through 14M, another alternative intermediate connection mount 809 is provided. The connection mount 809 generally has the same features as the connection mount 709 depicted in FIGS. 14H through 14J except the tabs 805 are modified to reduce the cost and complexity of manufacturing the snap lock feature associated with the connection mount 809. As shown in FIG. 14M, the connection mount 809 includes a plurality of tabs 805 unevenly distributed about the periphery of the distal section 801. The tabs 805 are symmetric about the cross-sectional plane defining the cross section depicted in FIG. 14L and include an upper tab 805A and two lower tabs 805B, 805C. The lower tabs 805B, 805C each include an outer side surface 853 that is substantially tangential to the outer circumference of the base wall 815 of the recess 807 and which are substantially parallel to each other. The substantially tangential and substantially parallel configuration of the side surfaces 853 reduces the cost and complexity of manufacturing the lower tabs 805B, 805C without sacrificing mechanical strength of the snap-fit joint between the intermediate connection mount 809 and the ring electrode 103.

In some implementations, a multi-piece mold may be used to form the tabs 805. The substantially tangential configuration of the side surfaces 853 of the lower tabs 805B, 805C may enable the use of a two-piece or half-shell mold. Each half of the mold can be radially removed from the intermediate connection mount 809 after formation of the tabs 805 in opposing directions parallel to the outer side surfaces 853 of the lower tabs 805B, 805C with relative ease. If the side surfaces 853 were formed at a lesser angle than tangential to the base wall 815 and not parallel to each other, release of the two-piece, or half-shell, mold from the tabs 805 may be difficult, which may result in damage to the intermediate connection mount 809 and/or the mold. Thus, in some implementations, e.g., in the embodiment of FIGS. 14H-J, a three-piece or a higher number mold may be used during manufacturing if the tabs 805 are not formed with the substantially tangential and parallel side surfaces 853. The three-piece or higher number mold may reduce damage to the parts, with the drawback of additional manufacturing pieces.

With reference to FIGS. 14N through 14P, another alternative intermediate connection mount 909 is provided. The connection mount 909 generally has the same features as the connection mount 109 depicted in FIGS. 14A and 14B except the distal section 901 has been modified to reduce the strength of the snap lock mechanism. The distal section 901 depicted in FIGS. 14N through 14P includes four tabs 605 evenly distributed about the periphery of the connection mount 909 and protruding radially outwardly from the base wall 915 of the recess 907. The tabs 905 collectively extend around a majority of the periphery of the distal section 901 to provide more joint strength than the tabs depicted in FIGS. 14E through 14M but less joint strength than the tabs 405 depicted in FIGS. 14A and 14B. Slots are formed between the tabs 905. The width of the slots may vary to provide a desired joint strength between the intermediate connection mount 909 and the ring electrode 103. The sidewalls 953 of the tabs 905 may extend approximately perpendicular relative to the base wall 915 of the recess 907, as shown in FIGS. 14N through 14P, or at oblique angles relative to the base wall 915.

The locking feature of the connection mount 909 may include any number of tabs 905. Generally, the distal section 901 of the connection mount 909 includes at least one tab 905, which may extend continuously or discontinuously around the periphery of the connection mount 909. The at least one tab 905 may extend around a minority or a majority of the circumference of the distal section 901 of the connection mount 909. The at least one tab 905 may have a suitable cross-sectional shape to provide a suitable interlock insertion and retention force. The at least one tab 905 may include a substantially square distal shoulder 913 to increase the mechanical strength of the mechanical snap-fit joint between the intermediate connection mount 909 and the ring electrode 103. At least one side surface of the at least one tab 905 may extend at an oblique angle, such as tangentially, from a circumferential surface of the distal section 901 to reduce the cost and/or complexity of manufacturing the locking feature of the intermediate connection mount 909, as previously discussed.

In addition to the helical anchor electrode 108, the spacer/stopper ring 113 and the seal ring 115 are mounted on the distal end of the tip electrode pin 105 that extends distally beyond the distal fitting 374 of the intermediate connection mount 109. The spacer/stopper ring 113 is placed about the medial shaft section 304 of the tip electrode pin 105 adjacent the medial annular flange 310. The spacer/stopper 113 may be made of an electrically insulating material to reduce potential electrode electrical "chatter" that is known to occur in prior art designs with metallic components used in the control of advancement and retraction. For example, the spacer/stopper 113 may be made of polyethylene, polyether ether ketone (PEEK), or polysulfone, and may have a hardness of Shore 80 in order to provide appropriate flexibility to fit around the medial shaft section 304 and appropriate resiliency to be retained thereon. The diameter of the spacer/stopper 113 is slightly less than the inner diameter of the tip housing 110 in which it and the helical anchor electrode 108 are ultimately housed. In this manner, as the helical anchor electrode 108 is advanced out of and retracted into the tip electrode 106, the spacer/stopper 113 can slide within the sleeve bore 328 of the tip housing 110 and around the medial shaft section 304 of the tip electrode pin 105 while helping maintain axial alignment of the helical anchor electrode 108 within the tip housing 110.

The distal and proximal travel of the helical anchor electrode 108 is limited by the spacer/stopper 113 in combination with the proximal annular flange 307 and the medial annular flange 310. The spacer/stopper 113 interfaces with the flat face 387 of the distal fitting 374 of the intermediate connection mount 109 when pushed upon by the medial annular flange 310 to arrest proximal travel of the helical anchor electrode 108. The spacer/stopper 113 also interfaces with the sleeve shoulder 329 between the sleeve bore 328 and the narrower diameter middle bore 332 of the tip housing 110 when pushed by the proximal annular flange 307 to arrest distal travel of the helical anchor electrode 108.

The seal ring 115 is stretched over the distal annular flange 312 to reside on the seal shaft section 306 between the medial and distal annular flanges 310, 312. The seal ring 115 is positioned within the middle bore 332 of the tip housing 110 and is configured to interface with the inner wall defining the middle bore 332 to provide a fluid-tight seal. The inner diameter of the cylindrical section 391 is designed to fit against the seal shaft section 306. The radius entrance 398 to the center aperture 396 from the distal side of the seal ring 115 helps reinforce the seal with respect to the seal shaft section 306 on the tip electrode pin 105 as well as provide for easy release of the core molding pin during manufacturing. The angled design of the radial wall 393 on the outer diameter also helps reinforce the seal against the middle bore 332. The seal ring 115 remains within and travels along a length of the middle bore 332 for all positions of the helical anchor electrode 108 and as it is advanced or retracted, thereby maintaining the fluid-tight seal at all times while also providing for a low friction force on the middle bore 332.

The marker band 111 may be molded separately and then insert molded into the tip bore 338 during the molding process for the tip housing 110. Two opposing ones of the four sidewall retention holes 322 are positioned to allow molding material of the tip housing 110 to flow into and around the marker band 111, thus providing a form for the retention posts 331, the outer diameter of the guide walls 334, the diameter for the tip bore 338 and the shelf shoulder 335 of the tip housing 110. The marker band 111 is thereby held in place within the tip bore 338 by the retention posts 331. The other two sidewall retention holes 322 remain clear during the insert molding process, are aligned with the retention apertures 330 formed in the tip housing 110, and are provided for accepting the two retention plugs 348a/b of the soft tip plug 117.

The soft tip plug 117 also fits within the tip bore 338 such that the arcuate walls 346a/b fit between the guide walls 334 in the tip bore 338 of the tip housing 110. The retention plugs 348a/b fit within the retention holes 322 of the marker band 111 and the retention apertures 330 of the tip housing 111 to retain the soft tip plug 117 on the distal end of the tip housing 110. The complicated geometry of the bond between the soft tip plug 117 and the tip housing 110 is configured to be sufficiently strong to carry any mechanical loads during implantation and ensure long term life in the heart. In some implementations, the soft tip plug 117 may receive a steroid capsule (e.g., dexamethasone) or other medicament.

The sleeve bore 328 of the tip housing 110 fits over and bonds to the distal fitting 374 of the intermediate connection mount 109. The tip housing 110 may be bonded to the distal fitting 374 with a friction fit, medical adhesive, or both to ensure that the tip housing 110 is permanently affixed to the lead 100. The tip housing 110 provides a housing for the helical anchor electrode 108 in the retracted position during lead insertion in the patient. Once the distal end 104 of the lead is in place, the tip housing 110 provides several features central to the functionality of the implantation of the helical anchor electrode 108 into myocardial tissue. As shown in FIGS. 10B and 10C, the anchor guide 336 in the tip housing 110 is positioned between adjacent windings of the helical anchor electrode 108. In order to extend or advance the helical anchor electrode 108 beyond the soft tip plug 117, the physician rotates the connector pin 112 at the proximal end 102 of the lead 100 clockwise. The rotational motion of the connector pin 112 is translated along the length of the inner conductor coil 120 to the tip electrode pin 105, which further translates the rotation to the helical anchor electrode 108. Because the anchor guide 336 is positioned between the windings of the helical anchor electrode 108, the helical anchor electrode 108 is advanced distally as it rotates rather than merely rotating in a constant longitudinal position.

As the connector pin 112 is rotated by the physician, the tip electrode pin 105 advances distally within the intermediate connection mount 109 and the tip housing 110 as the helical anchor electrode 108 interfacing with the anchor guide 336 functions as a worm drive. The medial shaft section 304 of the tip electrode pin 105 slides through the cylindrical aperture 391 of the spacer/stopper 113 until the proximal annular flange 307 reaches the spacer/stopper 113 and begins to push it distally. The tip electrode pin 105, and thus the helical anchor electrode 108 are able to advance distally because the inner conductor coil 120 is a coil and can thus expand slightly along its length as the helical anchor electrode 108 advances with respect to the anchor guide 336, which remains in a stationary position within the tip housing 110. The extension of the helical anchor electrode 108 is arrested when the spacer/stopper 113 interfaces with the sleeve shoulder 329 of the tip sleeve 110 as shown in FIG. 10C and blocks further distal advancement of the proximal annular flange 307 of the tip electrode pin 105. At this point, the helical anchor electrode 108 should be sufficiently embedded within the endocardial tissue to hold the active electrode tip 106 permanently in place without completely perforating the wall of the heart.

If the helical anchor electrode 108 needs to be retracted, e.g., for repositioning or removal of the lead 100, the physician can rotate the connector pin 112 counterclockwise at the proximal end 102 of the lead 100. This counterclockwise movement is translated along the length of the inner conductor coil 120 to the tip electrode pin 105, which further translates the rotation to the helical anchor electrode 108. Because the anchor guide 336 is positioned between the windings of the helical anchor electrode 108, the helical anchor electrode 108 acts as a worm drive and is retracted proximally as it rotates rather than merely rotating in a constant longitudinal position. The retraction of the helical anchor electrode 108 is arrested when the spacer/stopper 113 interfaces with the distal fitting 374 of the intermediate connection mount 109 and blocks further proximal movement of the medial annular flange 310 of the tip electrode pin 105. At this point, the helical anchor electrode 108 should be fully retracted and housed within the tip housing 110 and no further retraction is necessary. In this way, the windings of the helical anchor electrode 108 remain engaged with the anchor guide 336. If the helical anchor electrode 108 were to be retracted too far such that there was no longer an interface with the anchor guide 336, the helical anchor electrode 108 could not be advanced or retracted and would merely rotate in the same longitudinal position.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification, examples and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. Many of the implementations described herein are not required and the order of steps or operation may be a matter of choice, dependent on the performance requirements of the particular implementation. Accordingly, the operations making up the embodiments of the technology described herein may be referred to variously as methods, operations, or steps. It should be understood that operations may be performed in any order, unless explicitly claimed otherwise or a specific order is inherently necessitated by the claim language. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. An intermediate connection mount for use with a distal end of an active cardiac lead and connectable with a ring electrode located proximally of the intermediate connection mount, the intermediate connection mount comprising
   a medial separator;
   a distal fitting extending from the medial separator in a distal direction; and
   a proximal fitting extending from the medial separator in a proximal direction and connectable to the ring electrode, the proximal fitting including at least one radially-extending tab spaced from the medial separator to define an annular recess between the at least one tab and the medial separator, wherein
   the at least one radially-extending tab comprises a plurality of protrusions, the plurality of protrusions being spaced evenly around a circumference of the proximal fitting, and wherein:
   at least two of the plurality of protrusions each includes a first side surface having a width extending at a tangent from to a surface of the proximal fitting and the first side surfaces of the at least two of the plurality of protrusions are parallel to each other.

2. The intermediate connection mount of claim 1, wherein the at least one tab extends around the periphery of a proximal section of the intermediate connection mount.

3. The intermediate connection mount of claim 2, wherein the at least one tab includes a chamfered proximal surface, a substantially square distal shoulder, and a substantially cylindrical surface located intermediate the proximal surface and the distal shoulder.

4. The intermediate connection mount of claim 1, wherein the proximal fitting further includes alternating ridges and channels spaced from the at least one tab in a proximal direction.

5. The intermediate connection mount of claim 4, wherein the distal fitting includes alternating ribs and channels.

* * * * *